(12) United States Patent
Zelickson et al.

(10) Patent No.: US 9,032,576 B2
(45) Date of Patent: May 19, 2015

(54) APPARATUS WITH ELLIPTICAL MOVEMENT FOR MICRODERMABRASION AND TOPICAL DELIVERY OF TREATMENTS

(71) Applicant: Newton Medical, LLC, Minneapolis, MN (US)

(72) Inventors: Brian David Zelickson, Minneapolis, MN (US); Nathaniel Hayes Freeman, Missoula, MT (US); Kevin John Thompson, Chaska, MN (US); Michael Joseph Wayman, Waconia, MN (US); Shawn Michael Filipek, Prior Lake, MN (US); Alvin Sheldon Zelickson, Golden Valley, MN (US)

(73) Assignee: NEWTON MEDICAL, LLC, Minneapolis, MN (US)

( * ) Notice: Subject to any disclaimer, the term of this patent is extended or adjusted under 35 U.S.C. 154(b) by 0 days.

(21) Appl. No.: 13/964,099

(22) Filed: Aug. 11, 2013

(65) Prior Publication Data

US 2014/0202493 A1 Jul. 24, 2014

Related U.S. Application Data

(60) Provisional application No. 61/739,453, filed on Dec. 19, 2012.

(51) Int. Cl.
*A46B 13/02* (2006.01)
*A46B 13/04* (2006.01)
(Continued)

(52) U.S. Cl.
CPC ............... *A46B 13/02* (2013.01); *Y10T 16/05* (2015.01); *A47K 7/043* (2013.01); *B24B 23/03* (2013.01);
(Continued)

(58) Field of Classification Search
USPC ................ 15/21.1, 22.1, 28, 29, 97.1; 74/86; 173/170, 213, 214, 217; 451/270, 271, 451/357, 359; 601/15, 17, 18, 84, 85, 87, 601/89, 93, 95, 97, 101, 103, 112, 114, 601/DIG. 1, DIG. 2, DIG. 5
See application file for complete search history.

(56) References Cited

U.S. PATENT DOCUMENTS 2,250,975 A * 7/1941 Sussman ......................... 15/22.1
2,774,292 A * 12/1956 Hartmann ....................... 172/40
(Continued)

FOREIGN PATENT DOCUMENTS

DE        2015973 A1   10/1970
WO    2005091748 A2   10/2005
(Continued)

OTHER PUBLICATIONS

Search report for International Patent Application No. PCT/US2013/76110; May 2, 2014.
(Continued)

*Primary Examiner* — Mark Spisich
(74) *Attorney, Agent, or Firm* — Jason A. Bernstein; Barnes & Thornburg LLP

(57) ABSTRACT

A device for providing elliptical path motion to skin or other surface. The device includes a motor, shaft, and a cam having at least one offset axis cam lobe for creating offset motion. A mounting bracket assembly that has a pair of arms associated with the motor can be moved by the cam in an elliptical path having X-axis, Y-axis and, in exemplary embodiments, Z-axis movement. The mounting bracket assembly may have two brackets, each being associated with an oscillating plate. Each oscillating plate may have a plurality of protrusions or tufts of bristles protruding therefrom. Elliptical movement of the oscillating plates creates offset elliptical motion of the protrusions associated with each oscillating plate. A fluid delivery system may be incorporated to provide fluid through the device. The device may be used for cleaning, stimulation or treatment of skin.

40 Claims, 41 Drawing Sheets

(51) Int. Cl.
| | | |
|---|---|---|
| *A47K 7/04* | (2006.01) | |
| *A61H 7/00* | (2006.01) | |
| *A61H 23/02* | (2006.01) | |
| *F16H 25/18* | (2006.01) | |
| *B23Q 5/04* | (2006.01) | |
| *F21V 33/00* | (2006.01) | |
| *A61N 5/06* | (2006.01) | |
| *B24B 23/03* | (2006.01) | |
| *B24B 23/04* | (2006.01) | |
| *A61M 35/00* | (2006.01) | |

(52) U.S. Cl.
CPC ......... *B24B 23/04* (2013.01); *A46B 2200/1006* (2013.01); *A46B 2200/102* (2013.01); *A61H 2201/1207* (2013.01); *A61H 2201/1481* (2013.01); *F16H 25/18* (2013.01); *A46B 13/04* (2013.01); *B23Q 5/046* (2013.01); *F21V 33/0084* (2013.01); *A61M 35/003* (2013.01); *A61H 7/005* (2013.01); *A61H 23/0254* (2013.01); *A61H 2201/10* (2013.01); *A61H 2201/105* (2013.01); *A61H 2201/1215* (2013.01); *A61H 2201/1418* (2013.01); *A61H 2201/501* (2013.01); *A61H 2201/5015* (2013.01); *A61N 5/0616* (2013.01); *A61N 2005/0651* (2013.01); *A61N 2005/0654* (2013.01)

(56) References Cited

U.S. PATENT DOCUMENTS

| | | | | |
|---|---|---|---|---|
| 2,893,177 | A | * | 7/1959 | Bruck .................. 451/356 |
| 3,699,952 | A | | 10/1972 | Waters et al. |
| 4,027,348 | A | * | 6/1977 | Flowers et al. ........... 15/22.1 |
| 5,069,586 | A | | 12/1991 | Casey |
| 5,569,168 | A | | 10/1996 | Hartwig |
| 5,830,177 | A | | 11/1998 | Li et al. |
| 6,080,127 | A | | 6/2000 | Li et al. |
| 6,200,281 | B1 | * | 3/2001 | Frajdenrajch ............ 601/84 |
| 6,252,333 | B1 | | 6/2001 | Iino et al. |
| 6,645,184 | B1 | | 11/2003 | Zelickson et al. |
| 6,766,199 | B2 | | 7/2004 | Cook et al. |
| 7,044,938 | B2 | | 5/2006 | La Bianco et al. |
| 7,090,649 | B2 | | 8/2006 | Kang |
| 7,104,873 | B1 | * | 9/2006 | Borinato et al. ........... 451/159 |
| 7,157,816 | B2 | | 1/2007 | Pilcher et al. |
| 7,305,269 | B2 | | 12/2007 | Cook et al. |
| 7,320,691 | B2 | | 1/2008 | Pilcher et al. |
| 7,354,423 | B2 | | 4/2008 | Zelickson et al. |
| 7,384,377 | B2 | | 6/2008 | Berman |
| 7,384,405 | B2 | | 6/2008 | Rhoades |
| 7,386,906 | B2 | | 6/2008 | Roth et al. |
| 7,789,092 | B2 | | 9/2010 | Akridge et al. |
| 8,052,662 | B2 | | 11/2011 | Zelickson et al. |
| 8,343,116 | B2 | | 1/2013 | Ignon et al. |
| 8,484,788 | B2 | | 7/2013 | Brewer et al. |
| 8,522,383 | B2 | | 9/2013 | Hulli |
| 8,641,702 | B2 | | 2/2014 | Pilcher et al. |
| 2004/0147984 | A1 | | 7/2004 | Altshuler et al. |
| 2004/0225239 | A1 | | 11/2004 | Yamamoto et al. |
| 2005/0125919 | A1 | | 6/2005 | Fattori |
| 2005/0278876 | A1 | | 12/2005 | Roth et al. |
| 2007/0123808 | A1 | | 5/2007 | Rhoades |
| 2008/0097355 | A1 | | 4/2008 | Pilcher et al. |
| 2008/0146977 | A1 | | 6/2008 | Hilditch |
| 2009/0234338 | A1 | | 9/2009 | Roth et al. |
| 2009/0234341 | A1 | | 9/2009 | Roth |
| 2009/0234343 | A1 | | 9/2009 | Behrakis |
| 2009/0306577 | A1 | | 12/2009 | Akridge et al. |
| 2010/0048101 | A1 | * | 2/2010 | King et al. .................. 451/28 |
| 2010/0049177 | A1 | | 2/2010 | Boone, III et al. |
| 2011/0084097 | A1 | | 4/2011 | Gueret |
| 2011/0087158 | A1 | | 4/2011 | Cole et al. |
| 2011/0184499 | A1 | | 7/2011 | Radi |
| 2012/0016380 | A1 | | 1/2012 | Zelickson |
| 2012/0165710 | A1 | | 6/2012 | Nichols |
| 2012/0192366 | A1 | | 8/2012 | Cobabe et al. |
| 2012/0260931 | A1 | | 10/2012 | Martin et al. |
| 2013/0023901 | A1 | | 1/2013 | Sanchez-Martinez et al. |
| 2013/0060176 | A1 | | 3/2013 | Nichols |
| 2013/0079689 | A1 | | 3/2013 | Thierman |
| 2014/0013525 | A1 | | 1/2014 | Zhou |
| 2014/0058300 | A1 | | 2/2014 | Ungemach et al. |

FOREIGN PATENT DOCUMENTS

| | | | |
|---|---|---|---|
| WO | 2008098646 | A1 | 8/2008 |
| WO | 2008098647 | A1 | 8/2008 |
| WO | 2008098648 | A1 | 8/2008 |
| WO | 2008098649 | A1 | 8/2008 |
| WO | 2008098650 | A1 | 8/2008 |
| WO | 2008098651 | A1 | 8/2008 |
| WO | 2009/049185 | * | 4/2009 |
| WO | 2012097409 | A1 | 7/2012 |
| WO | 2012122083 | A1 | 9/2012 |

OTHER PUBLICATIONS

Appeal brief filed in U.S. Appl. No. 12/056,649; Apr. 13, 2012.
Examiner's Answer in U.S. Appl. No. 12/056,649; May 25, 2012.
Reply Brief filed in U.S. Appl. No. 12/056,649; Jul. 24, 2012.
Office Action in U.S. Appl. No. 11/969,447; May 21, 2012.

* cited by examiner

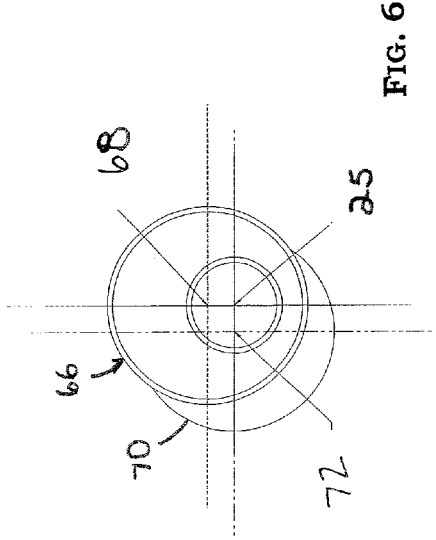
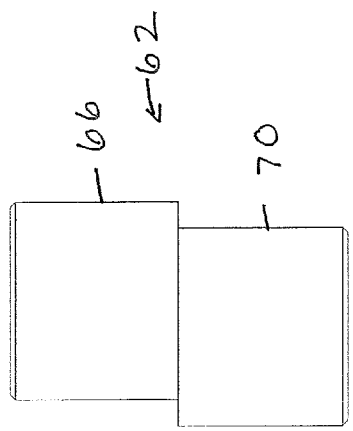
FIG. 6
FIG. 5

FIG. 43
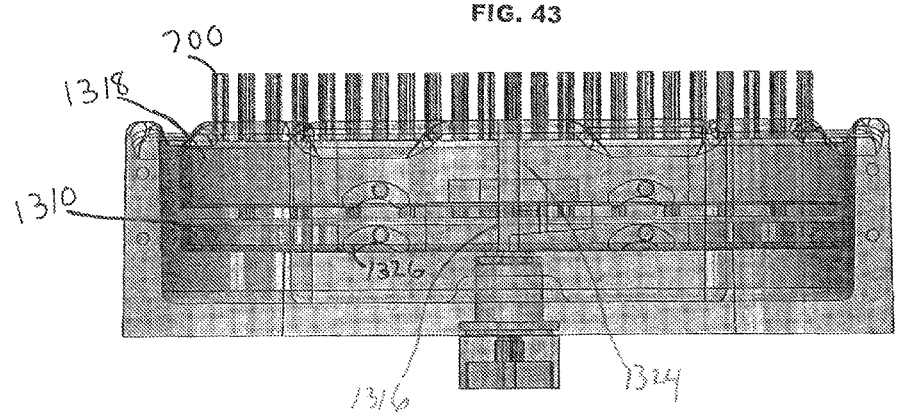
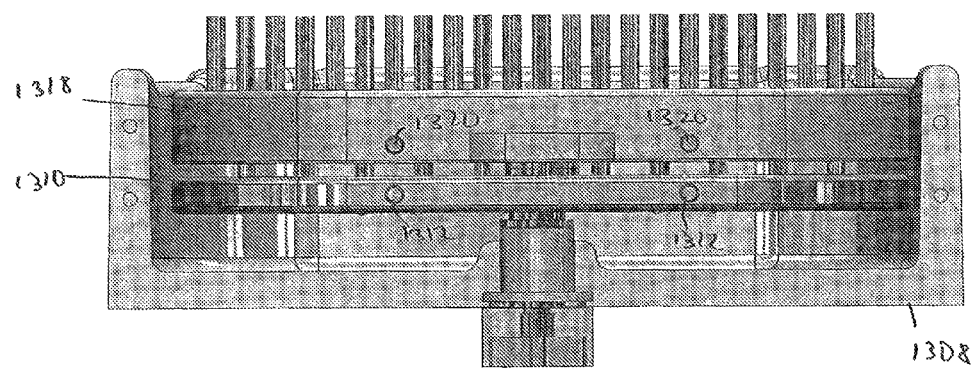
FIG. 44

APPARATUS WITH ELLIPTICAL MOVEMENT FOR MICRODERMABRASION AND TOPICAL DELIVERY OF TREATMENTS

CROSS-REFERENCE TO RELATED APPLICATION

This application claims benefit of U.S. provisional patent application No. 61/739,453, filed Dec. 19, 2012, entitled "Microdermabrasion Brush, Fluid Dispersion System and Rejuvenating Red and Infrared Light" and commonly assigned to the assignee of the present application, the disclosure of which is incorporated by reference in its entirety herein.

FIELD

The present disclosure relates, in exemplary embodiments, to mechanical apparatus for cleaning, stimulating or applying a treatment to skin or other surfaces.

BACKGROUND

The skin is the largest organ of the body and as such can lead to multiple types of medical and cosmetic conditions that at times need maintenance and or treatments. These include cleansing of the skin, protecting the skin from environmental elements such as ultraviolet rays to help prevent photo-aging and sunburns, preventing the skin from developing conditions such as inflammatory conditions such as eczema or infections, and enhancing the cosmetic appearance of the skin by increasing or decreasing the amount of hair on certain areas of the skin.

To date there are multiple ways to address the variety of these conditions which include either topical applications such as skin lotions, foams, gels or serums which can cleanse, protect, prevent or repair the skin. There are devices which produce either mechanical energy such as cleansers, shavers, optical energy such as lights or lasers, heat in the form of ultrasound or microwave energy to address the many issues of the skin.

It would be desirable to have a device that could deliver stimulation, energy or treatments, including delivery of fluids, to skin or other surface.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to the more detailed description below.

In exemplary embodiments, an apparatus is disclosed for providing elliptical motion. The apparatus may comprise a motor; a drive shaft having an axis of rotation and extending from the motor, the shaft having a distal end; a motor housing associated with the motor; an elliptical motion creating mechanism associated with the shaft, the mechanism including an offset motion means for imparting rotational movement in a direction offset from the axis of the shaft. The apparatus may further comprise a mounting bracket including a base plate operatively associated with the offset motion means, the base plate having a first side defining an X-axis movement direction and a second side generally perpendicular to the first side, the second side defining a Y-axis movement direction, a first side arm extending from the base plate and associated with the motor housing, the first side arm having a distal end terminating in a connection portion, the first side arm defining a Z-axis movement direction, a second side arm extending from the base plate and associated with the motor housing, the second side arm having a distal end terminating in a connection portion. Rotation of the shaft causes the offset motion means for imparting movement to rotate and impart elliptical motion to the mounting bracket such that the base plate moves in an elliptical path in both the X-axis and Y-axis directions.

An apparatus for providing elliptical motion to a structure, comprising: a motor; a drive shaft having an axis of rotation and extending from the motor; means for generating at least one rotational motion having an axis offset from the shaft axis; and, means for providing oscillating elliptical motion associated with the means for generating rotational motion.

In exemplary embodiments, a device for skin cleansing or delivery of skin treatment, comprises a main housing; a motor; a drive shaft having an axis of rotation and extending from the motor; and, at least one attachment member associated with the motor. The apparatus further comprises an elliptical motion creating mechanism associated with the shaft, the mechanism including a first axially offset member for imparting movement in a first elliptical direction offset from the axis of the shaft and a second axially offset member for imparting movement in a second elliptical direction offset from the axis of the shaft. The apparatus further comprises a mounting bracket assembly comprising an inner mounting bracket having an inner base plate operatively associated with the first offset member, a first side arm extending from the inner base plate and associated with an attachment member, a second side arm extending from the inner base plate and associated with an attachment member, a first pin extending from the inner mounting bracket base plate. The mounting bracket assembly further includes an outer mounting bracket comprising an outer base plate operatively associated with the second offset member, a first side leg extending from the outer mounting bracket base plate, a second side leg extending from the outer mounting bracket base plate, and a second pin extending from the outer mounting bracket base plate, whereby rotation of the shaft causes the first offset member to rotate and impart oscillating elliptical motion to the inner mounting bracket and the first pin, and impart oscillating elliptical motion to the outer mounting bracket and the second pin. The device further may include a brush head assembly attachable to the main housing, the brush head assembly comprising a first oscillating plate having a first face including a connecting portion adapted to connect to the first connecting member, the first oscillating plate having a second face including a plurality of protrusions; a second oscillating plate having a first face including a connecting portion adapted to connect to the second connecting member, the first oscillating plate having a second face including a plurality of protrusions, wherein the first and second oscillating plates are in separate generally parallel planes and adapted for oscillating elliptical; a brush head assembly housing adapted to attach to the main housing; a first suspension ring associated with the first oscillating plate and the brush head assembly housing such that the first suspension ring permits movement of the first oscillating plate in the X- and Y-axes; and, a second suspension ring associated with the second oscillating plate and the brush head assembly housing such that the second suspension ring permits movement of the second oscillating plate in the X- and Y-axes.

Other features will become apparent upon reading the following detailed description of certain exemplary embodiments, when taken in conjunction with the appended claims.

BRIEF DESCRIPTION OF THE DRAWINGS

The drawings disclose exemplary embodiments in which like reference characters designate the same or similar parts throughout the figures of which:

FIG. 5 is a side view of an offset cam according to one exemplary embodiment.

FIG. 6 is a top plan view of the offset cam showing the axes of movement according to the exemplary embodiment of FIG. 5.

FIG. 43 is a side cutaway view of an oscillating plate and brush head assembly housing according to the exemplary embodiment of FIG. 41.

FIG. 44 is a side view in partial cutaway of an oscillating plate and brush head assembly housing according to the exemplary embodiment of FIG. 41.

DETAILED DESCRIPTION

Exemplary embodiments presented herein provide in one broad aspect a device for providing a structure moving in an elliptical path motion that can contact skin 5 or other surface to provide stimulation or treatment. In exemplary embodiments, a device is presented for providing motion having an elliptical path in the X-axis and Y-axis and further may have Z-axis movement, as well. In exemplary embodiments, a device is described for providing a brush formed of a plurality of protrusions, such as solid nibs or tufts of bristles, which protrusions can be driven in a multi-axis elliptical path to stimulate, abrade or otherwise affect a surface.

In exemplary embodiments, the surface may be skin, scalp, nail, tooth, gum, or other exposed area on a person or animal. The present disclosure also contemplates other surfaces being applicable, such as, but not limited to, floor, carpet, wood, metal, glass, fabric, hide, or any other material. In various exemplary embodiments skin is discussed as an example of a surface to be treated, but it is to be understood that any surface appropriate for the application can be used.

The term "treat" (including "treating," "treatment," "treated" and other forms thereof) as used herein is intended to broadly include, without limitation, one or more of contact, stimulate, massage, abrade, microdermabrade, cleanse, scrub, treat, apply or remove a substance, and other interactions or effects on a surface, but is not necessarily indicative of medical treatment.

Figure 18:
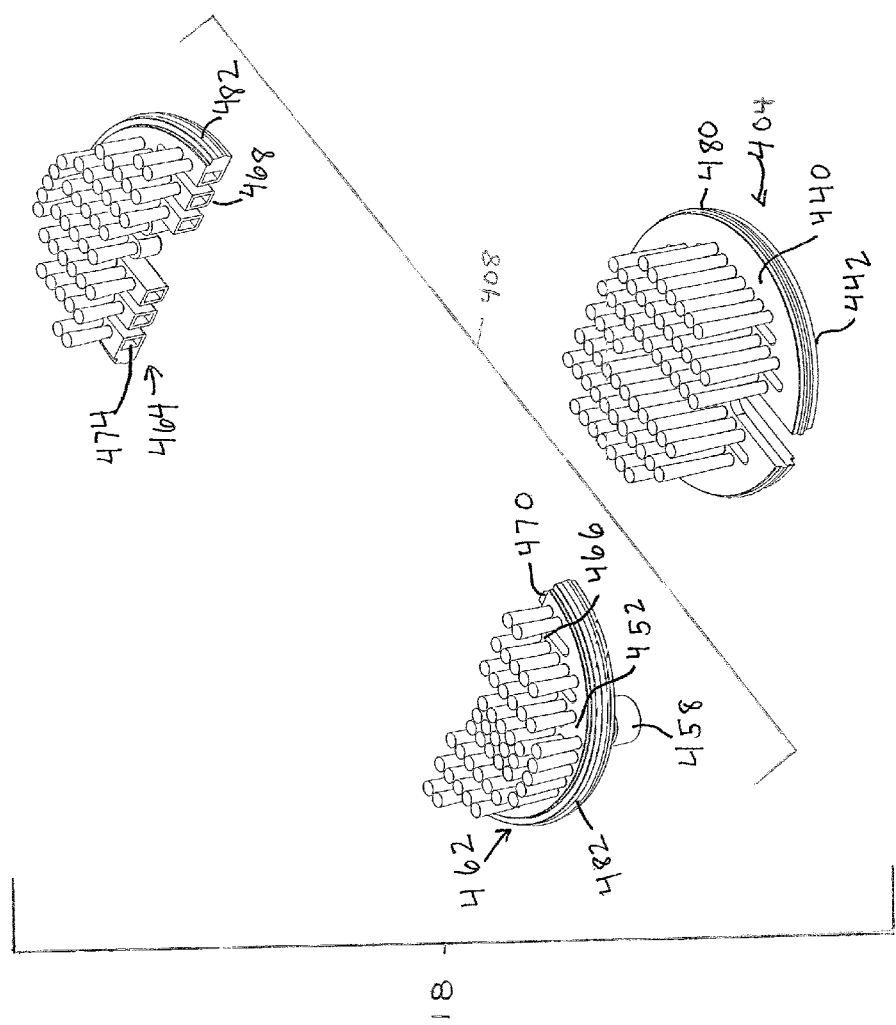
FIG. 18 is a schematic exploded top perspective view of a first oscillating plate and a second oscillating plate comprising two sections according the exemplary embodiment of FIG. 17.
Figure 19:
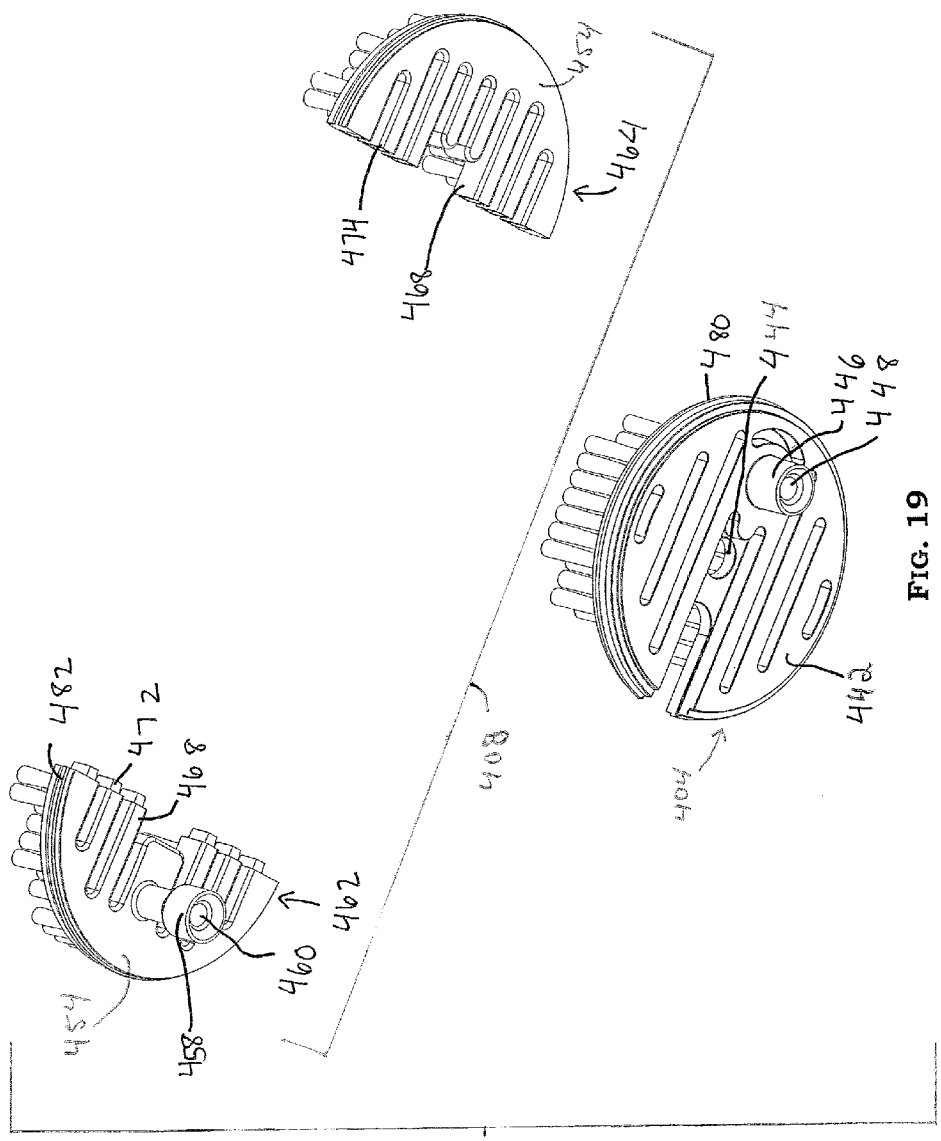
FIG. 19 is a schematic exploded bottom perspective view of a first oscillating plate and a second oscillating plate comprising two sections according to the exemplary embodiment of FIG. 17.
Figure 22:
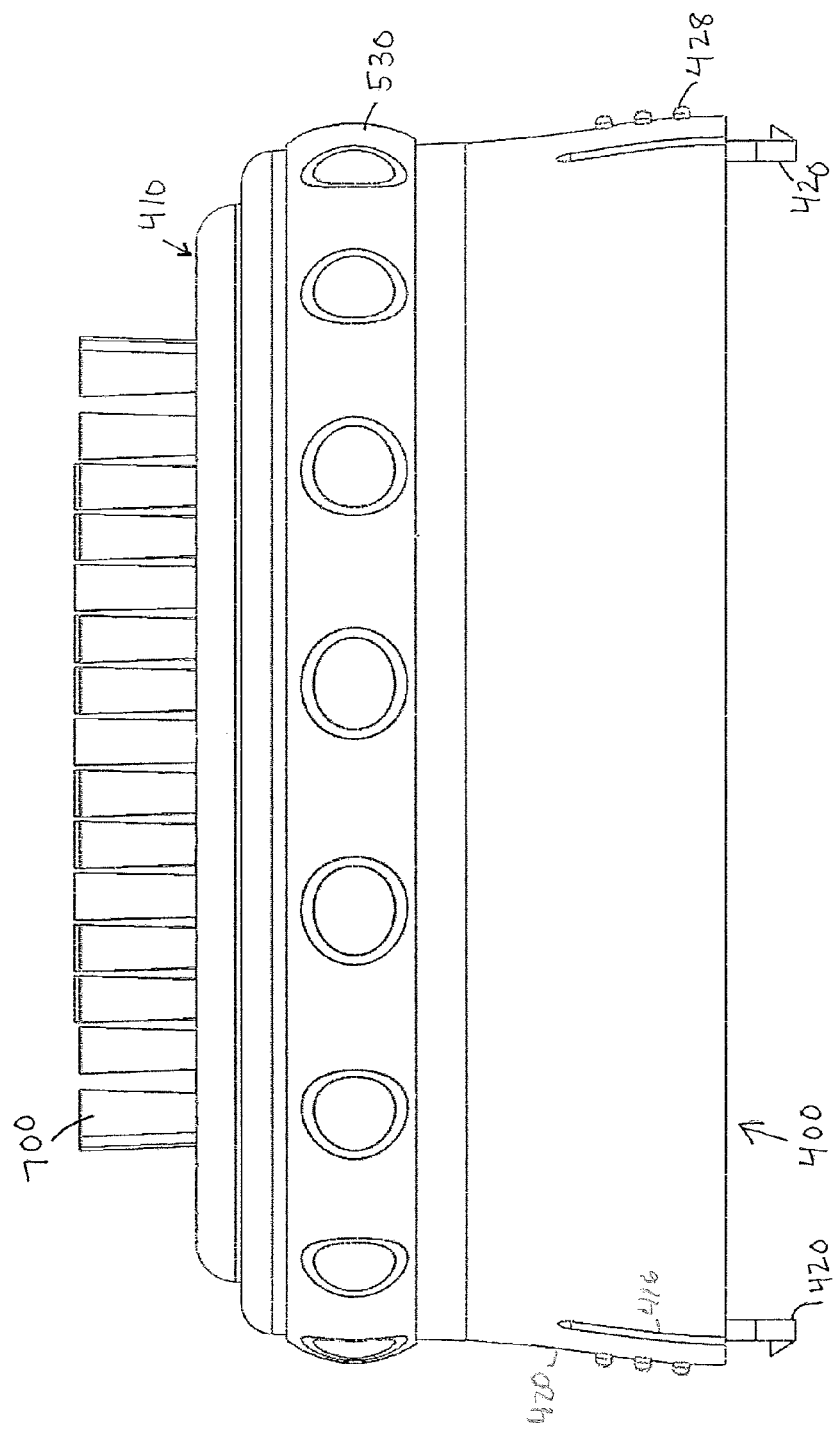
FIG. 22 is a side elevation view of a brush head assembly according to the exemplary embodiment of FIG. 17.

FIGS. 1-4 show one exemplary embodiment of a device 10 having main components of a main housing 12, a motor assembly 14, a mounting assembly 16 and an oscillating plate assembly 18 (shown in FIGS. 18-19). The main housing 12 contains the basic components of the device 10. In exemplary embodiments, the device 10 may also include one or more detachable head assemblies (generally referred to as element 20) (shown in, for example, FIGS. 22-24 as assembly 400, and FIG. 26 as assembly 600).

Figure 2A:
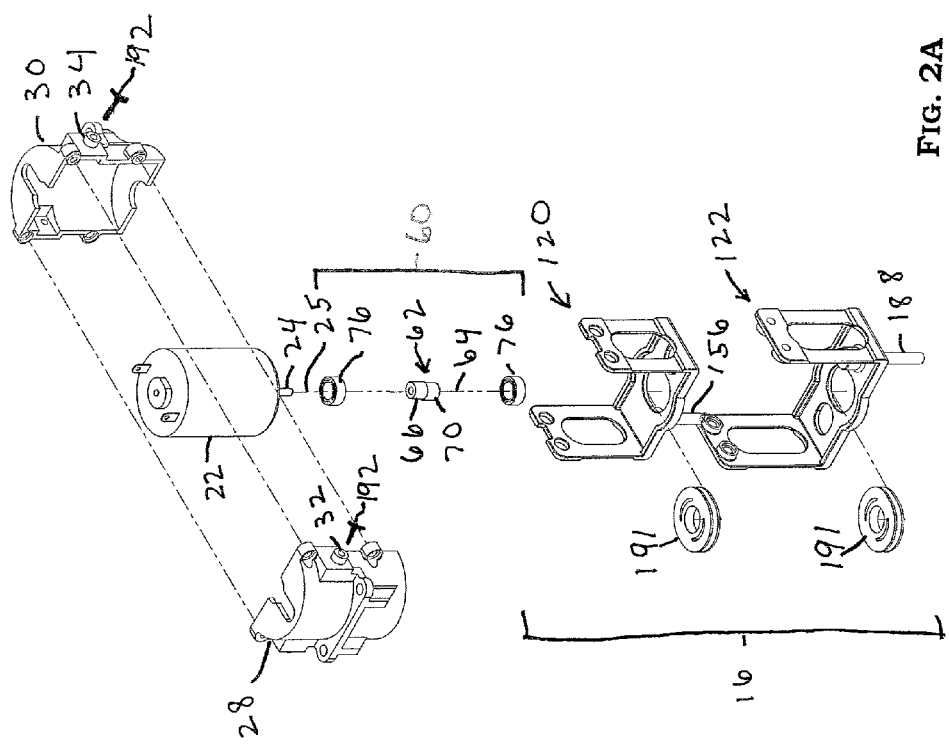
FIG. 2A is an exploded perspective view of the motor assembly and mounting bracket assembly according to the exemplary embodiment of FIG. 1 in which the mounting bracket arms are connected to the motor housing.
Figure 2B:
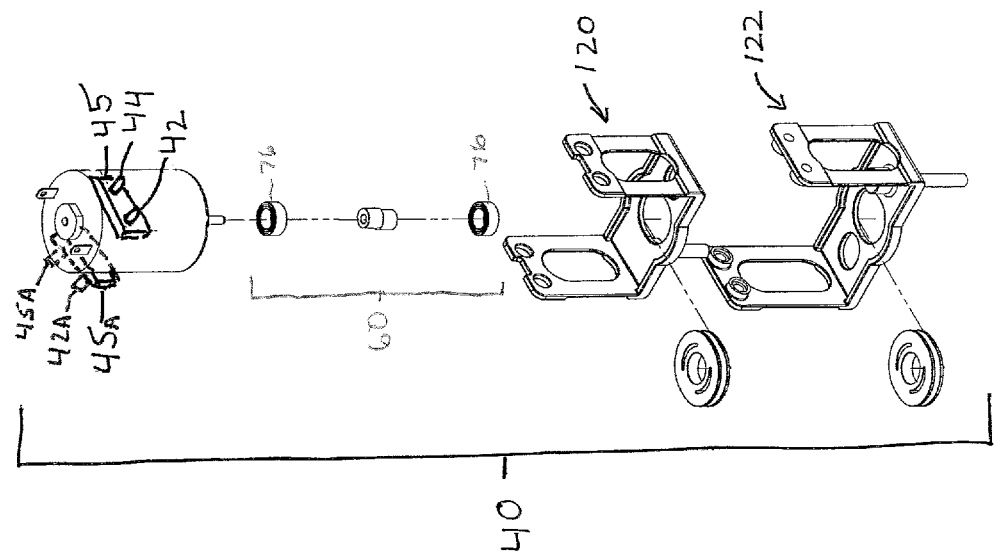
FIG. 2B is an exploded perspective view of a motor and mounting bracket assembly according to another exemplary embodiment in which the mounting bracket arms are connected to the motor.
Figure 3:
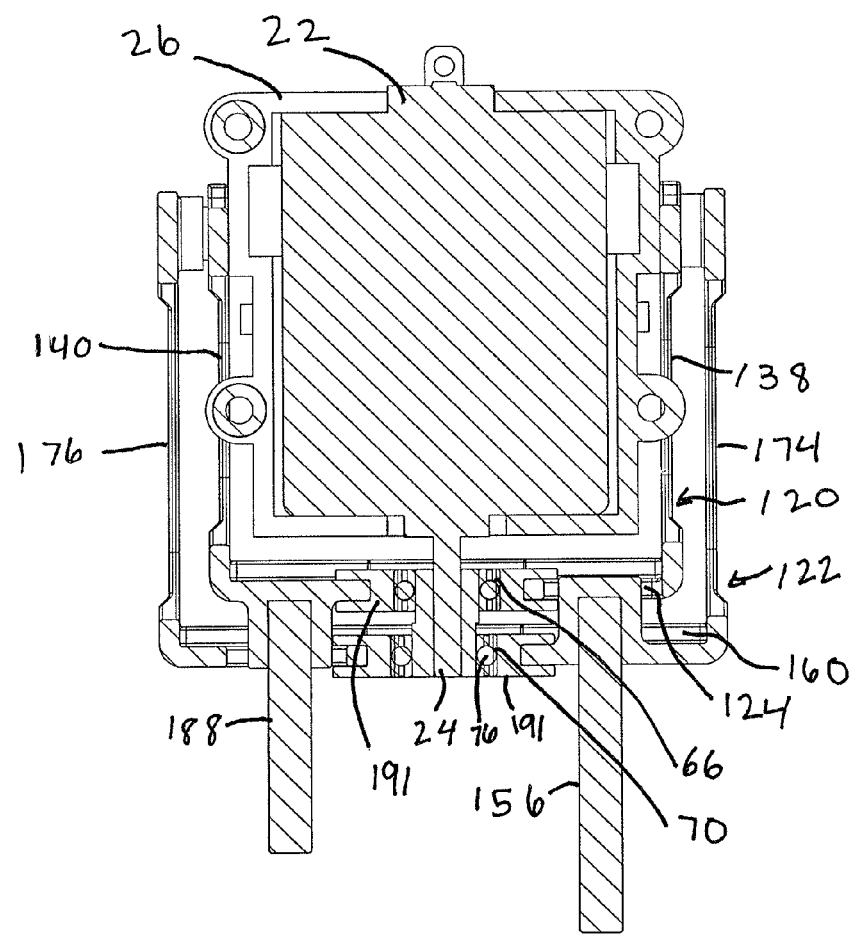
FIG. 3 is a side cutaway view of an assembled motor assembly and mounting bracket assembly according to the exemplary embodiment of FIG. 1.
Figure 4:
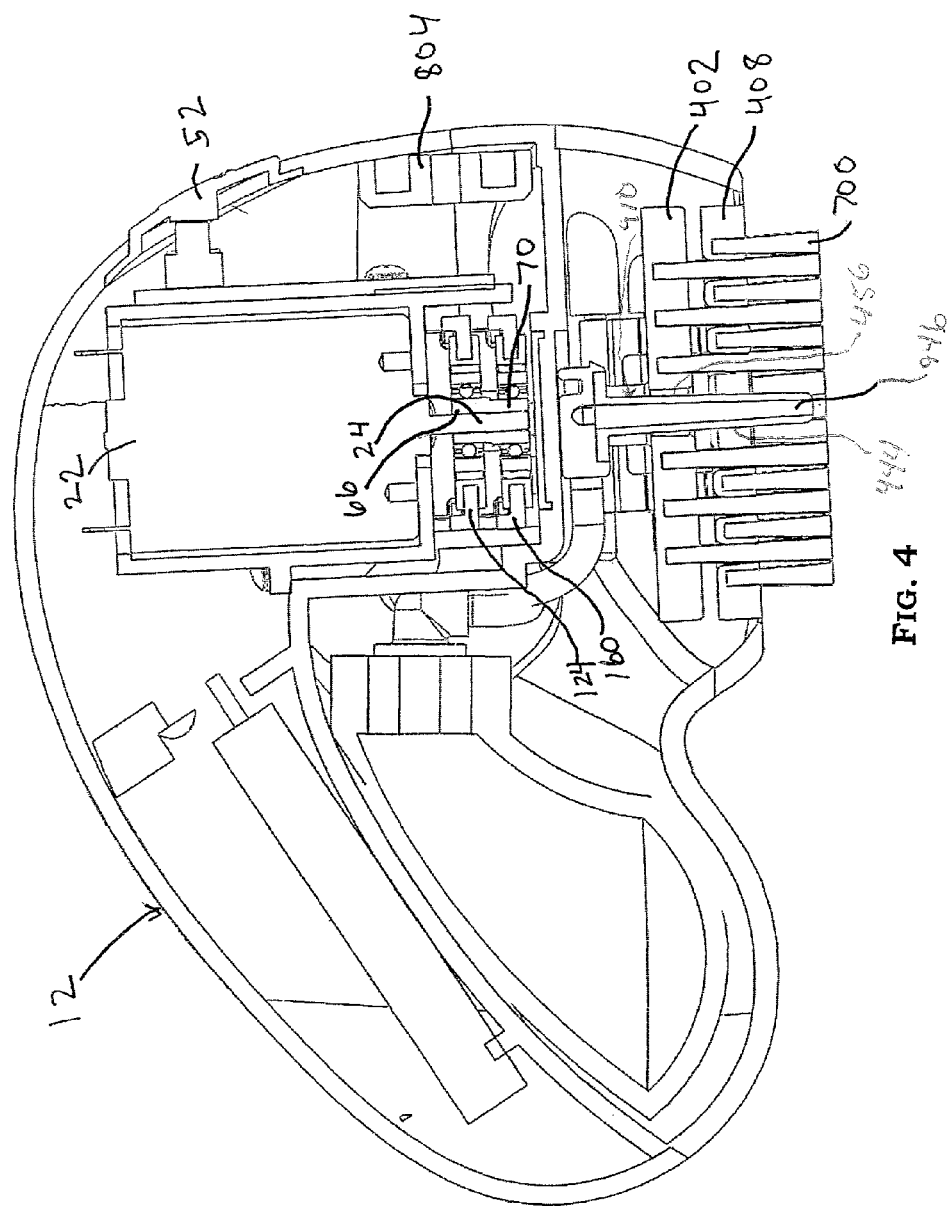
FIG. 4 is a side perspective view of an assembled motor assembly and mounting bracket assembly according to the exemplary embodiment of FIG. 1.

FIGS. 2A and 3 show one exemplary embodiment of a motor assembly 14 which includes a motor 22. The motor may be an AC, DC, brushless or other type of motor. In exemplary embodiments, the motor 22 is a DC brush motor. Extending from and driven by the motor 22 is a rotatable shaft 24, having an axis 25. In exemplary embodiments, the motor 22 may be at least partially housed in a motor housing 26. In exemplary embodiments, the motor housing 26 may comprise two mating portions 28, 30. In exemplary embodiments, each motor housing portion 28, 30 (attached to each other by fasteners 31) has a pair of bosses 32, 34 protruding from opposing sides thereof. FIG. 2B shows an alternative exemplary embodiment of a motor assembly 40 in which no motor housing 26 is used, and where the motor 22 itself may include a pair of connecting members 42, 44, such as, but not limited to, bosses, tubes, rings, pins, rods, screws, bolts, or the like, that are associated with opposing sides of the motor 22. In exemplary embodiments, as shown in FIG. 2B, the connecting members 42, 44 are associated with a plate 45. There also is a set of the connecting members 42A, 44A and optional plate 45A on a side of the motor opposite that of the connecting members 42, 44 and plate 45. FIG. 4 shows an exemplary embodiment of a motor assembly 14 as incorporated in one exemplary embodiment of a main housing 12.

The motor 22 may have an actuation mechanism 50 operatively associated therewith. In exemplary embodiments, the actuation mechanism 50 may be an on/off switch 52. In exemplary embodiments, the activation mechanism 50 can be at least one multi-position knob or switch that has different speed settings. Alternatively the activation mechanism may comprise an on/off switch, a speed controller, a pulse controller that can control pulsing on and off of the motor, or other feature.

In exemplary embodiments, an actuation microcontroller 54 (not shown) is in operable communication with the motor 22 and the actuation mechanism 50. The microcontroller 54 can control speed, pulse, charging and other features. The microcontroller 54 can detect the presence and type of head assembly 20 that is connected and can control features that are part of that assembly. In exemplary embodiments, the microcontroller 54 may incorporate a timer function that can be programmed to turn off the device after a preset amount of time. This may be useful in an application where a limited duration of exposure is needed, such as in the case where a light emitting head assembly (as described further hereinbelow) is used.

The device 10 may also include an audible tone generator or visual indicator, such as, but not limited to, a buzzer or other tone generator, or a light or other visual indicator to provide an indication of on/off, charge or other status or condition.

The shaft 24 is associated with an offset motion mechanism 60 for creating a dual offset elliptical motion. In exemplary embodiments, as shown in FIGS. 5-6 and also in FIGS. 2A, 2B, 3, and 4, the offset motion mechanism 60 may be a dual lobe cam 62. The cam 62 rotates about a central axis 64 which is aligned with the shaft axis 25. In exemplary embodiments, the cam 62 may comprise a first cam lobe 66 having an offset central axis 68 and having a second cam lobe 70 with an offset central axis 72. As illustrated in FIGS. 5-6 and 32-33, the central axis 68 of the first cam lobe 66 is offset from the shaft axis 25 so that the first cam lobe 66 rotates off axis from the shaft axis 25. Similarly, the central axis 72 of the second cam lobe 70 is offset from the shaft axis 25 so that the second cam lobe 70 rotates off axis from the shaft axis 25. The two cam lobe axes 68, 72 are offset from each other by, for example, but not by way of limitation, 90 degrees. Other offset amounts can be used. In exemplary embodiments, the first and second cam lobes 66, 70 may have offsets such as, but not limited to 0.010 and 0.005 inches, as measured from the center of the lobe to the center of the shaft 24. This distance creates the amount of offset motion, as described in greater detail hereinbelow.

Optionally, in exemplary embodiments, at least one bearing 76 fits over each cam lobe 68, 70. The bearing 76 may reduce friction, heat buildup, wear and/or noise.

Figure 7:
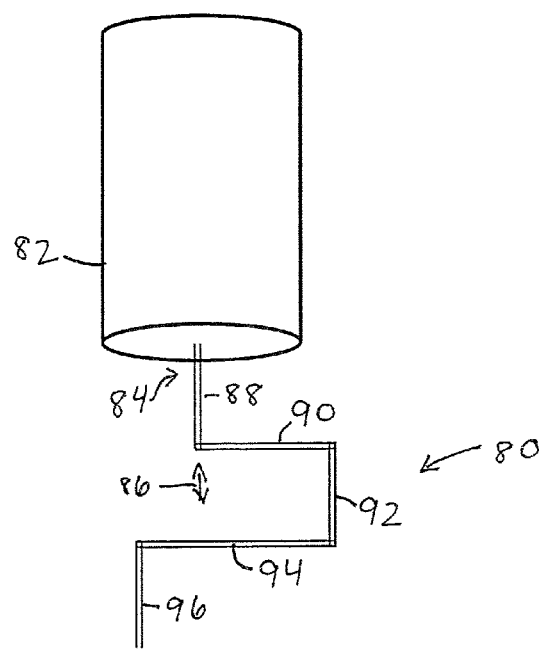
FIG. 7 is a schematic view of a motor and offset shaft mechanism according to a first alternative exemplary embodiment.

FIG. 7 shows an alternative exemplary embodiment of an offset motion mechanism 80 comprising a motor 82 and a shaft 84 having a central axis 86. The shaft 84 has a first portion 88 co-axial with the shaft axis 86, a second portion 90 having a length "L1" extending at an angle (such as, but not limited to, perpendicular) from the first portion 88, a third portion 92 extending from the second portion 90 and generally parallel to the shaft axis 86, a fourth portion 94 having a length "L2" and extending at an angle (such as, but not limited to, perpendicular) from the third portion 92 and optionally generally parallel to the second portion 90, and a fifth portion 96 extending from the fourth portion 94 and generally parallel to the first portion 88. L1 is either greater than or less than L2 so as to create the offset of the third portion 92 axis and the fourth portion 94 axis from the shaft central axis 86. A 90 degree offset may enhance motor efficiency and minimize and make more regular the load (torque) on the motor 82 exerted by the motion of the offset motion mechanism 80 and associated components, as described in greater detail hereinbelow.

Figure 8:
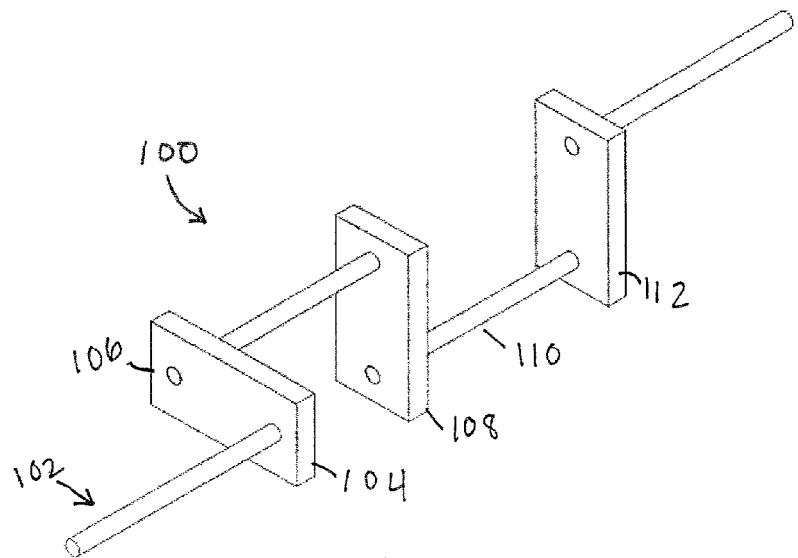
FIG. 8 is a schematic view of a motor and offset shaft mechanism according to a second alternative exemplary embodiment.

In another exemplary embodiment, shown in FIG. 8, offset motion mechanism 100 may a drive shaft 102 that is associated with an elongated first plate 104 having one end 106 associated with the shaft 102 and the other end 108 associated with a pivot pin 110. The pivot pin 110 is also associated with one end of a second plate 112. The angles of the two plates 104, 112 are offset with respect to each other.

Figure 1:
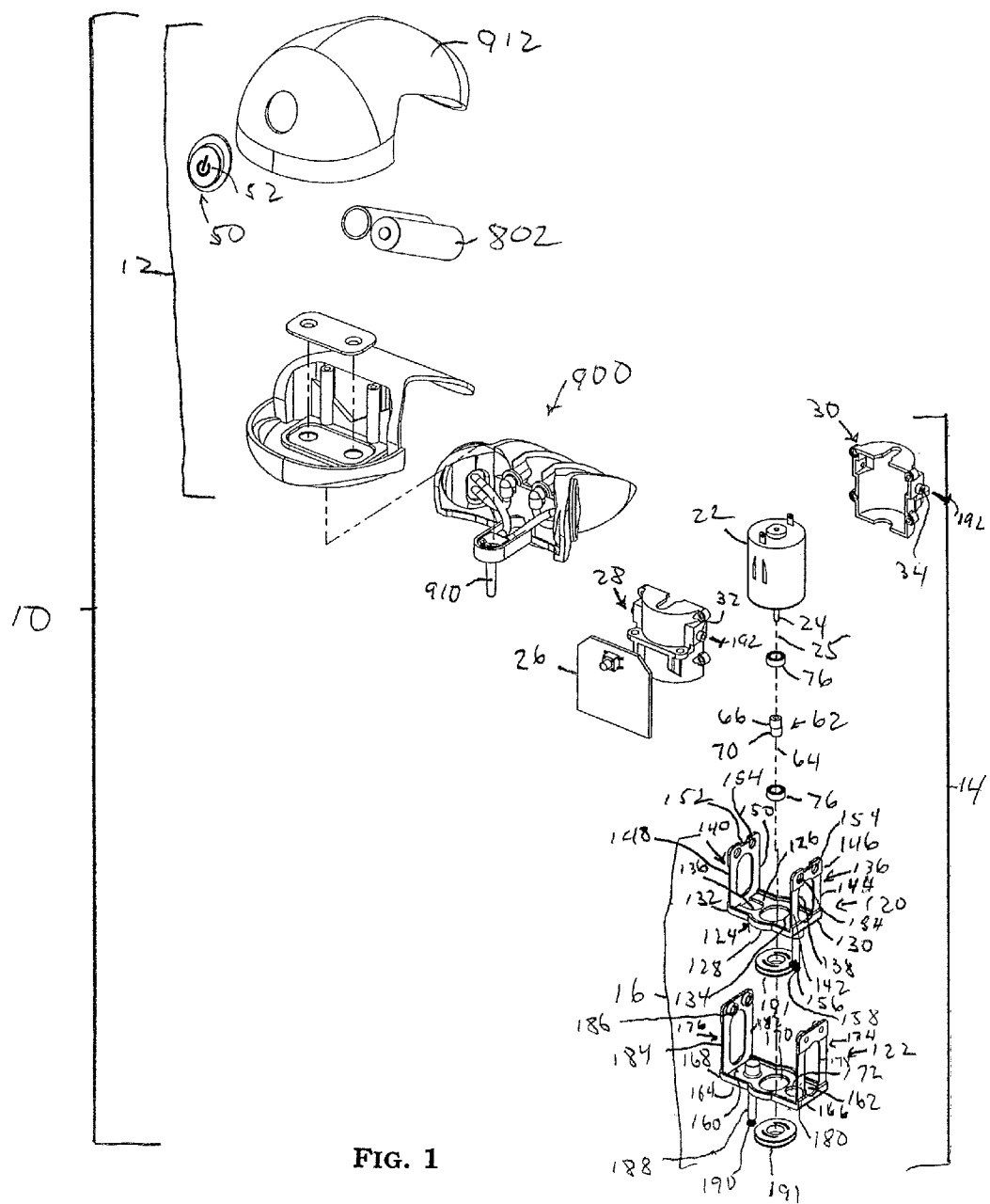
FIG. 1 is an exploded perspective view of the motor assembly, mounting plate assembly and fluid delivery system of a device according to one exemplary embodiment.

FIGS. 1-3 show an exemplary embodiment of a mounting bracket assembly 16 comprising an inner first mounting bracket 120 and an outer second mounting bracket 122. The inner first mounting bracket 120 has a base plate 124 having a top surface 126, a bottom surface 128, a first edge 130 and a second edge 132, as well as a central first aperture 134 and a second aperture 136 proximate to the first edge 130. A first side arm 138 extends generally perpendicularly from the first edge 130 of the base plate 124. A second side arm 140 extends generally perpendicularly from the opposing second edge 132 of the base plate 124 and generally parallel to the first side arm 138. In exemplary embodiments, at least one of the mounting brackets 120, 122 may be made of a material at least a portion of which is flexible or elastic.

In exemplary embodiments, as shown in FIGS. 1-4, the inner mounting bracket 120 first side arm 138 may have first and second leg portions 142, 144 and a cross beam 146 and the second side arm 140 may have first and second leg portions 148, 150, and a cross beam 152. Each of the four leg portions 142, 144, 148, 150 may have a distal end having an aperture 154 defined therein. The inner first mounting bracket 120 has a pin 156 extending generally perpendicularly from the base plate bottom surface 128 and proximate to the base plate second edge 132. The distal end of the pin 156 may terminate in a ball 158.

The outer second mounting bracket 122 has a base plate 160 having a top surface 162, a bottom surface 164, a first edge 166 and a second edge 168, as well as a central first aperture 170 and a second aperture 172 proximate to the second edge 168. A first side arm 174 extends generally perpendicularly from the first edge 166 of the base plate 160. A second side arm 176 extends generally perpendicularly from the opposing second edge 168 of the base plate 160 and generally parallel to the first side arm 174. In exemplary embodiments, the first side arm 174 may have first and second leg portions 178, 180 and the second side arm 176 may have first and second leg portions 182, 184. Each of the four leg portions 178, 180, 182, 184 may have a distal end having a setoff boss 186 associated therewith. The outer second mounting bracket 122 has a pin 188 extending generally perpendicularly from the base plate bottom face 164 and proximate to the base plate second edge 168. The distal end of the pin 188 may terminate in a ball 190.

A grommet 191 (described in detail hereinbelow) may be fitted in each of the central apertures 134, 170.

In assembling the mounting brackets 120, 122 and attaching them to the motor housing (in the exemplary embodiment shown in FIG. 2A), the inner first mounting bracket 120 is placed between the first and second side arms 174, 176 of the outer second mounting bracket 122 such that the pin 156 fits in the outer second mounting bracket second aperture 172 and the apertures 154 are aligned with the setoff bosses 186 of the legs of the outer second mounting bracket 122. The aligned apertures 154 and setoff bosses 186 are fitted over the bosses 32, 34 on the motor housing. A threaded screw 192 or other fastener passes through the apertures 154 and setoff bosses 186 holds each onto the motor housing 26. In the exemplary embodiment shown in FIG. 2B, the apertures 154 and setoff bosses 186 from the first side arms 138, 174 are connected to the connecting members 42, 44 and the apertures 154 and setoff bosses 186 from the second side arms 140, 176 are connected to the connecting members 42A, 44A.

Figure 9:
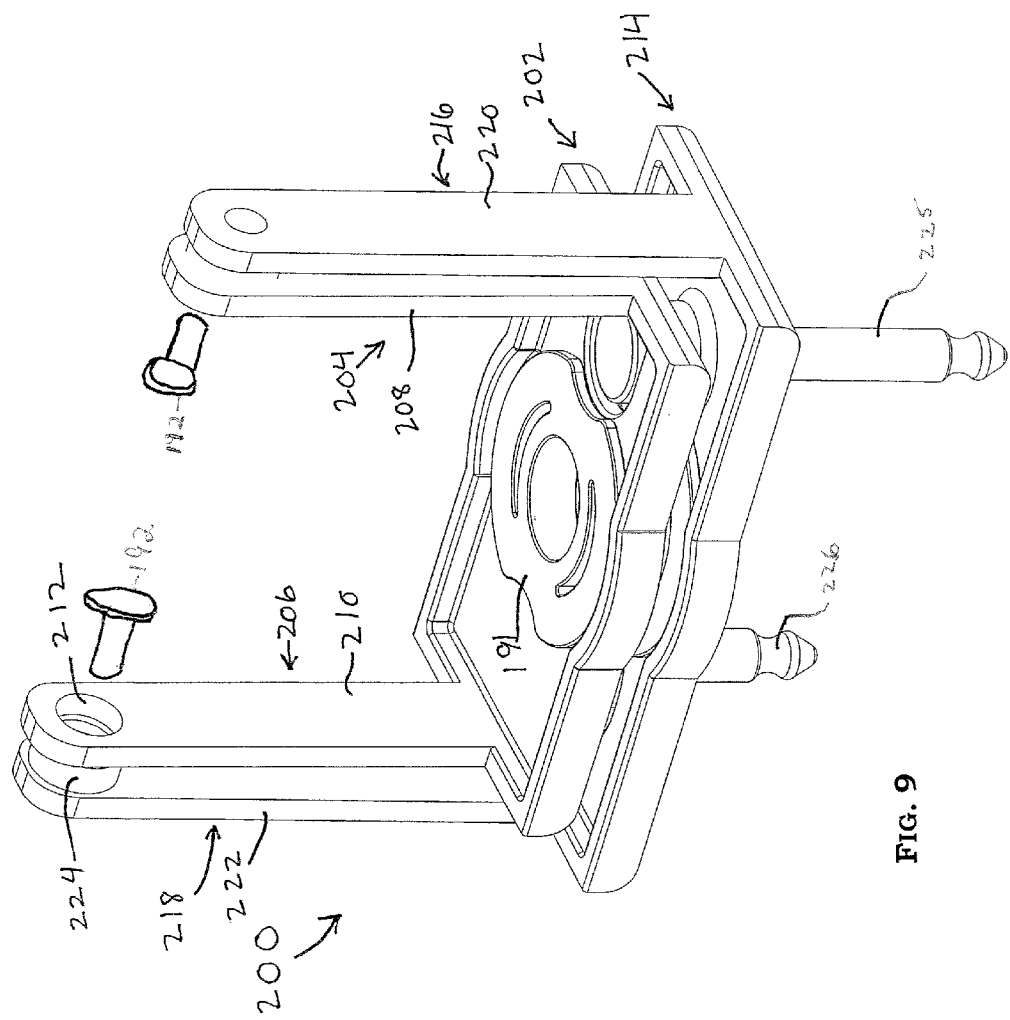
FIG. 9 is a perspective schematic view of a portion of a first inner mounting bracket and a second outer mounting bracket according to an alternative exemplary embodiment in which each mounting bracket has a single arm.

FIG. 9 shows an alternative exemplary embodiment of a mounting bracket assembly 200, an inner first mounting bracket 202 may have first and second side arms 204, 206 that may each include a single leg portion 208, 210 having a single aperture 212 defined in the distal end. An outer second mounting bracket 214 may have first and second side arms 216, 218 that may each include a single leg portion 220, 222 having a single setoff boss 224 associated with the distal end. Mounting bracket 202 has a pin 225 and mounting bracket 214 has a pin 226, both extending downward, similar to the pins 156, 188. The leg aperture 212 and leg boss 224 of each arm 204, 206 are connected to a motor housing setoff connecting member located on opposing sides of the housing by a single screw or other fastener 192, which may serve as a pivot point for the arms. Alternatively, where a motor housing is not used and the motor connecting members are associated with the motor or a plate (not shown, but generally similar in structure to the connecting members 42, 42A and plates 45 and 45A), the arms 204, 206 apertures 212 and boss 224 are associated with those connecting members.

Figure 10:
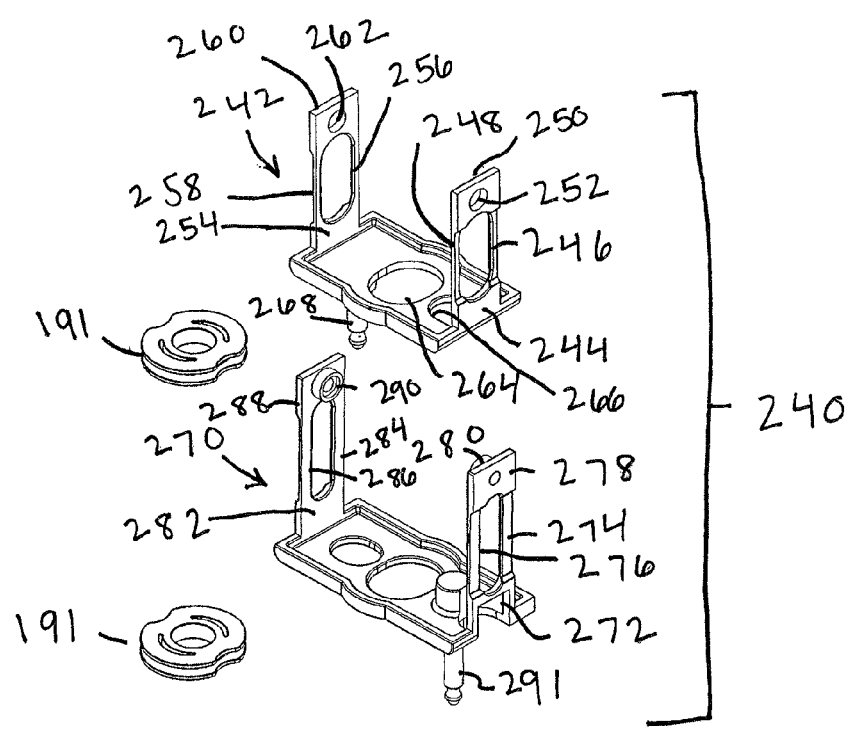
FIG. 10 is a perspective schematic view of a portion of a first inner mounting bracket and a second outer mounting bracket according to an alternative exemplary embodiment in which each bracket has two arms and a crossbar.
Figure 11:
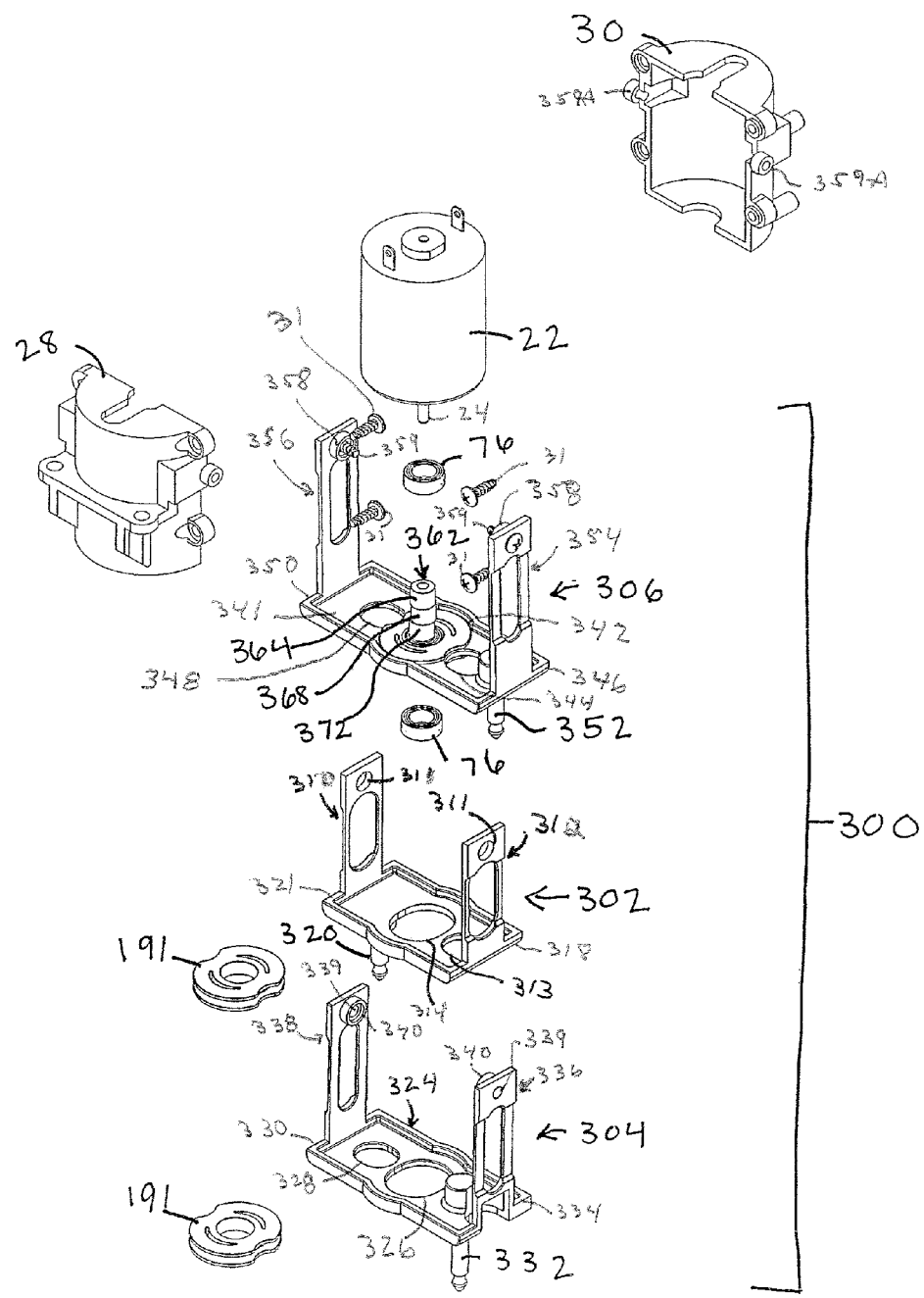
FIG. 11 is an exploded perspective view of a motor assembly and a mounting bracket assembly according to an alternative exemplary embodiment including three mounting plates.
Figure 12:
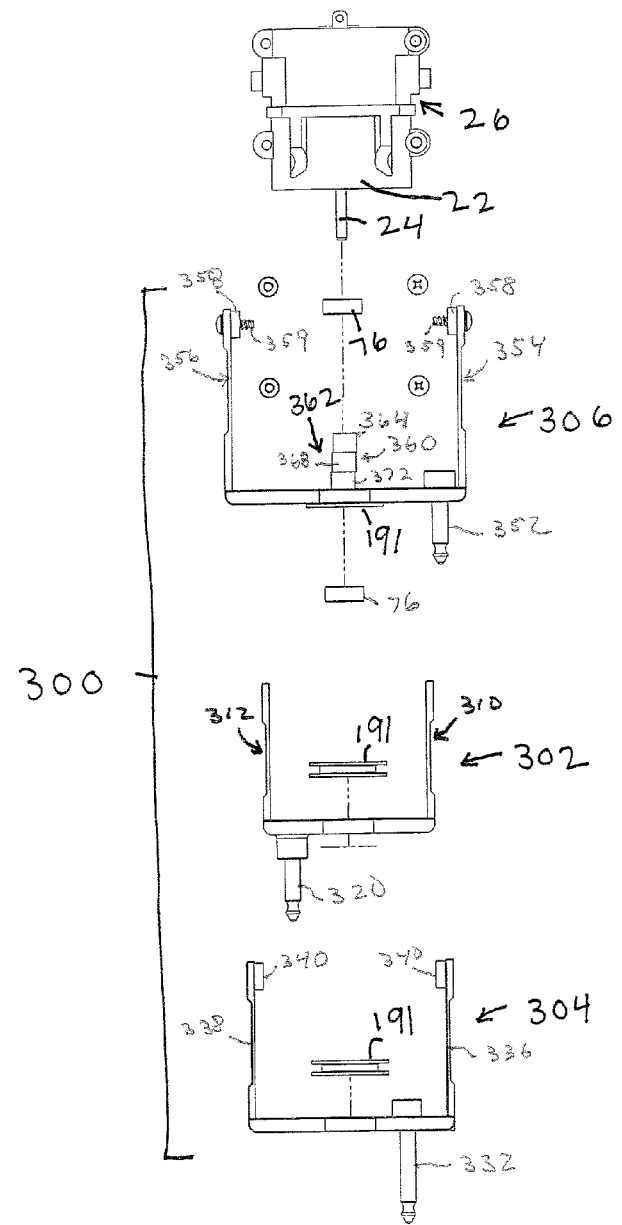
FIG. 12 is an exploded side elevation view of the motor assembly and a mounting bracket assembly according to the exemplary embodiment of FIG. 11.
Figure 13:
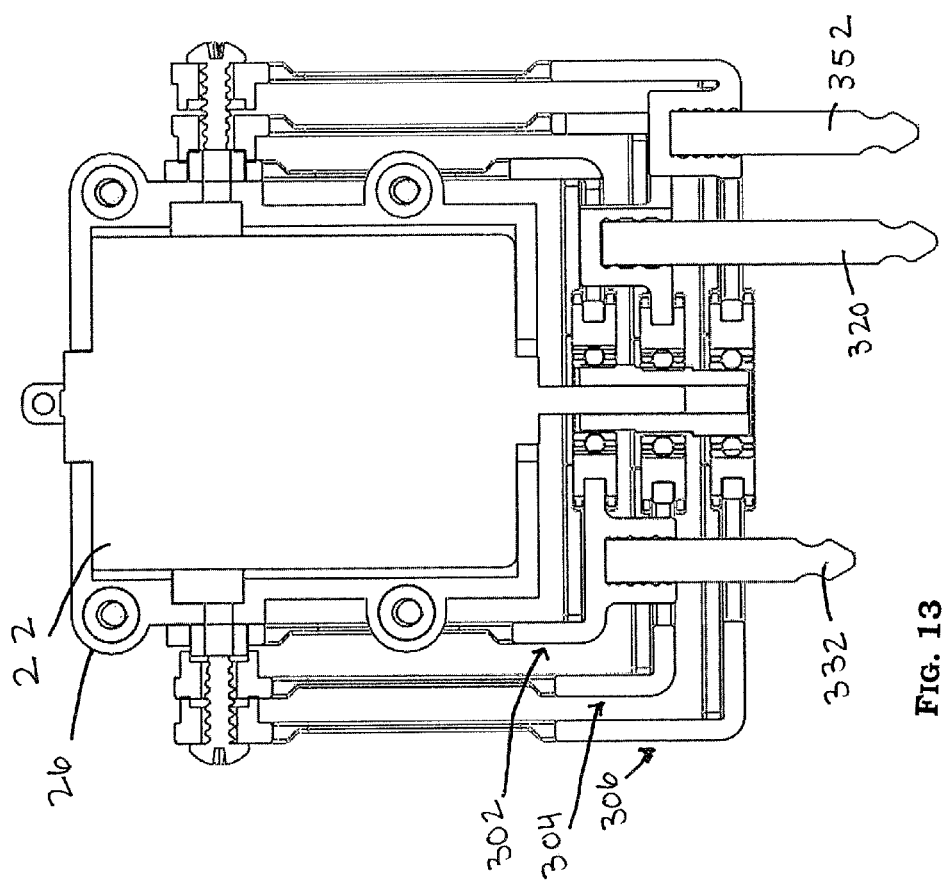
FIG. 13 is a side cutaway view of the motor assembly and a mounting bracket assembly according to the exemplary embodiment of FIG. 11.
Figure 14:
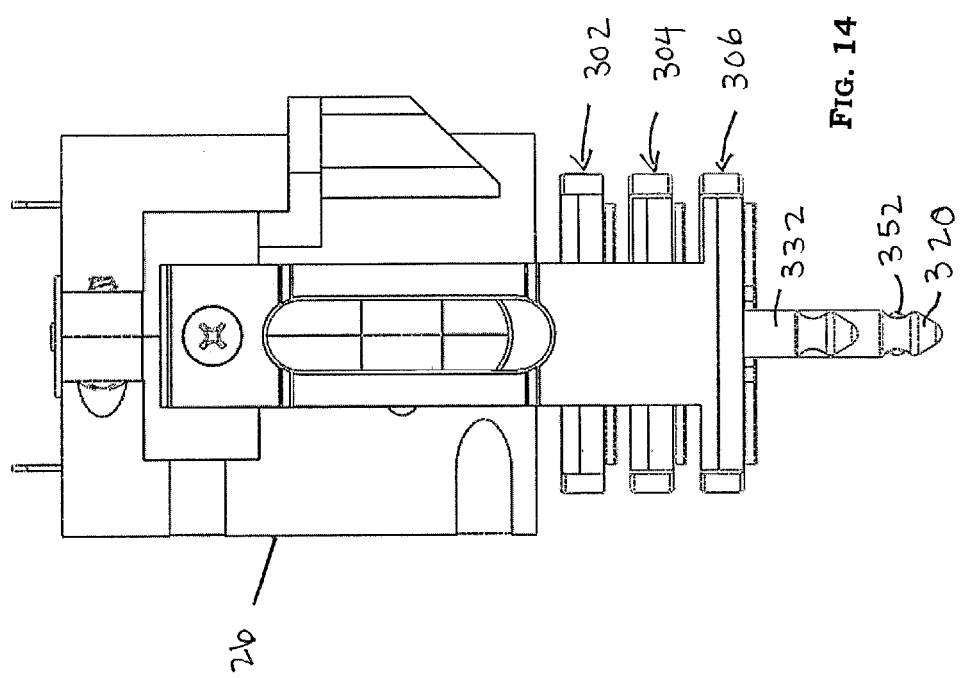
FIG. 14 is a side elevation view of the motor assembly and a mounting bracket assembly according to the exemplary embodiment of FIG. 11.

FIG. 10 shows another alternative exemplary embodiment of a mounting bracket assembly 240 having an inner first mounting bracket 242 having a first arm 244 comprising a first leg 246 and a second leg 248 that each have their distal end connected by a crossbar 250 having an aperture 252 formed therein. A second arm 254 is similarly constructed with first and second legs 256, 258, crossbar 260 and aperture 262. The inner first mounting bracket has a central aperture 264, second aperture 266 and pin 268, similar to exemplary embodiments described hereinabove. An outer second mounting bracket 270 has first arm 272 having a pair of first and second legs 274, 276 that are connected at their distal ends by a crossbar 278 having a boss 280. A second arm 282 has first and second legs 284, 286 connected by a crossbar 288 having a boss 290. A pin 291 extends from the base plate. The crossbar aperture and crossbar boss are connected to the motor housing or motor connecting member similar to the mounting bracket assembly 200 as described hereinabove.

FIGS. 11-15 show one alternative exemplary embodiment of mounting bracket assembly 300 having three mounting brackets 302, 304, 306. In exemplary embodiments, the first mounting bracket may have arms 310, 312 similar in structure to the arms 244, 254 described hereinabove and each arm has an aperture 311. The arm 312 may have a cutout portion 313 proximate to its base. The first mounting bracket 302 also has a central aperture 314, second aperture 316 proximate to a first edge 318, and a pin 320 extending downward proximate to a second edge 321. The second mounting bracket 304 has a base plate 324 having a central aperture 326, second aperture 328 proximate to a second edge 330 and a pin 332 extending downward from proximate to a first edge 334. In exemplary embodiments, the second mounting bracket 304 may have arms 336, 338 similar in structure to the arms 272, 282 described hereinabove, with the difference being that the distal end of each arm has an aperture 339 and a boss 340. The third mounting bracket 306 has a base plate 341 having a central aperture 342, a second aperture 344 proximate to a first edge 346, a third aperture 348 proximate to a second edge 350 and a pin 352 extending downward from proximate to the first edge 346. The third mounting bracket 306 has aims 354, 356 each having a setoff boss 358.

A motor 22 is associated with a motor housing 26 or, alternatively, a motor housing may not be used. The motor 22 has a shaft 24 extending therefrom. An offset motion creating mechanism may comprise an offset axis cam 360 having a central axis 362 and including a first cam lobe 364 having a first offset axis 366, a second cam lobe 368 having a second offset axis 370 and a third cam lobe 372 having a third offset axis 374. Each cam lobe has an offset axis offset from the central axis 362 of the offset axis cam 360. In exemplary embodiments, a bearing 76 may be fitted over a least a portion of each cam lobe. Each of the cam lobes may be fitted in the aperture of a grommet 191.

The mounting bracket assembly 300 is assembled as follows. The first mounting bracket 302 is placed inside the aims of the second mounting bracket 304, with the pin 320 passing through the central aperture 326. The arm apertures 311 are aligned with the bosses 340. The first and second mounting brackets 302, 304 are placed inside the arms of the third mounting bracket, with the pin 332 passing through the aperture 344 and the pin 320 passing through the third aperture 348. The arm apertures 311 and bosses 340 are aligned with the bosses 358 of the third mounting bracket arms 354, 356 and are secured by a fastener 359 or other pivot member which is associated with a bore 359A in opposite sides of the housing 30 such that each of the three mounting brackets 302, 304, 306 can pivot about the fastener 359.

The first cam lobe 364 fits in the grommet 191 in the third mounting bracket base plate central aperture 342. The second cam lobe 368 fits in the grommet 191 in the second mounting bracket base plate central aperture 326. The third cam lobe 372 fits in the grommet 191 in the first mounting bracket base plate central aperture 314.

Figure 15:
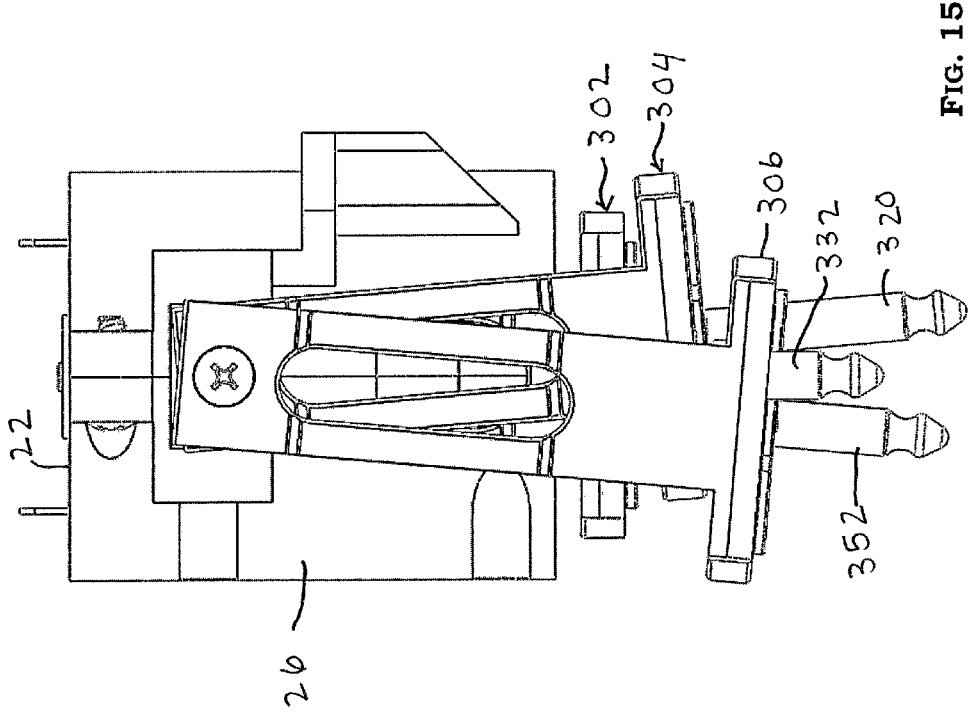
FIG. 15 is a side elevation view of the motor assembly and a mounting bracket assembly according to the exemplary embodiment of FIG. 14, showing (exaggerated) the pins offset.

FIG. 15 shows in an exaggerated fashion the motion of the mounting brackets 302, 304, 306 as the cam lobes 364, 368, 372 rotate. Each of the pins 320, 332, 352 can move in an elliptical path distinct from the other pins. Each of the pins may have a movement component in the Z-axis direction, in other words, in the general direction of the pin axis. The elliptical path movement is discussed in greater detail hereinbelow.

Changing the length or configuration of any of the pairs of side arms in the above-described mounting bracket assembly embodiments may result different elliptical movement, as discussed in greater detail hereinbelow.

Figure 16:
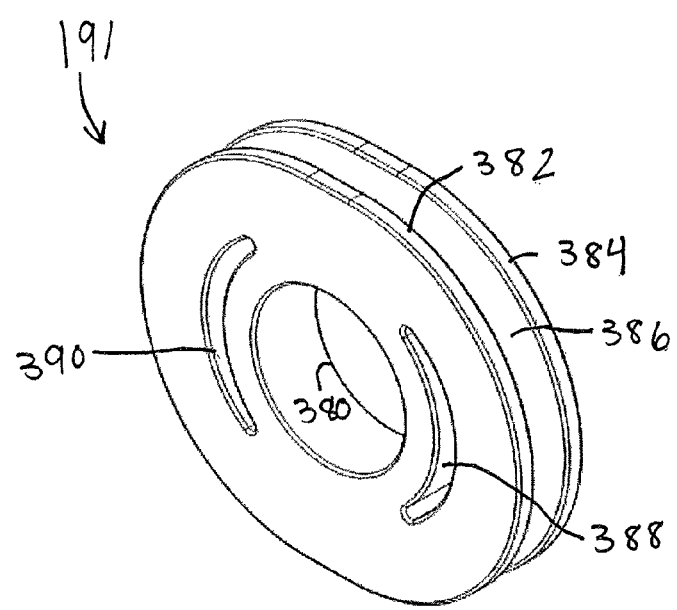
FIG. 16 is a perspective view of a grommet according to one exemplary embodiment.

In exemplary embodiments, the grommet 191 fits into the central aperture in each of the base plate as described herein in various exemplary embodiments. One exemplary embodiment of a grommet 191 is shown in FIG. 16. In exemplary embodiments, each central aperture in the mounting plates described hereinabove is oval or elliptical in shape. In an alternative exemplary embodiment, the base plate central aperture may be circular in shape. The grommet 191 may have an oval, elliptical, circular or other cross-section shape. In exemplary embodiments, the grommet 191 has a central bore 380 and may have an upper and a lower flange 382, 384 creating a recessed groove 386 that may fit and be retained in the bracket central aperture. In exemplary embodiments, the bore 380 extends all the way through the grommet 191. In other exemplary embodiments, the bore 380 extends only partially through the grommet. In exemplary embodiments, the grommet 191 is made of a material having some degree of elasticity or deformability, such as, but not limited to, silicone elastomer. The grommet 191 may have portions that have greater elasticity or deformability than other portions. For example, in one exemplary embodiment, the grommet 191 may have higher elasticity portions on opposing sides that are more elastic or deformable than less elastic portions on other opposing sides. In exemplary embodiments, shown in FIG. 16, the grommet 191 may include a pair of cutout portions 388, 390 that create areas of greater elasticity or deformability. In exemplary embodiments, different properties of the grommet material may be adjusted to provide different effects on the elliptical motion (as described in greater detail hereinbelow). Higher elasticity or deformability may provide greater movement of the pins than lower elasticity or deformability. For example, the durometer (stiffness) of the grommet material may be changed. Alternatively, the shape or thickness of the material may be modified. Alternatively, portions of the grommet material may be thicker than other portions, the thicker portions being less elastic or deformable than the thinner portions. Alternatively, the grommet 191 may be made of more than one material, each material having different elasticity or deformability properties. It is to be understood that the elasticity or deformability of the grommet 191 could be altered by other means known to those of ordinary skill in the art. In exemplary embodiments, rather than the grommet 191 having flanges 382, 384, it may be co-molded or co-formed directly into the central aperture of the mounting plate when the plate is formed.

In exemplary embodiments, the first grommet fits within the central aperture in the mounting plate, for example, such as is shown in FIG. 9. In exemplary embodiments, the less elastic or deformable portion at opposing sides of the grommet are oriented to be aligned with the first and second sides of the base plate. In exemplary embodiments, a cam lobe fits at least partially within the grommet bore 380. In exemplary embodiments, the bearing 76 fits at least partially within the grommet bore 380.

In exemplary embodiments, the device 10 is constructed to accommodate one or more different types detachable head assemblies 20, each head having a distinct set of functions or features. Each head may have distinct applications or uses. Applications include, but are not limited to, cleaning, microdermabrasion, light therapy, topical delivery of fluids, hair removal, pigment reduction, sweat reduction, pain management, and the like. Alternatively, the device 10 may include a head that is permanently connected to the main housing.

FIGS. 17-25 show exemplary embodiments of a brush head assembly 400 incorporating a suspension ring and oscillating plate attachment mechanism. In exemplary embodiments, the brush head assembly 400 includes a head assembly housing 402, a first oscillating plate 404, a first suspension ring 406, a second oscillating plate 408, and a second suspension ring 410. The brush head assembly 400 may be manufactured separate from the device 10.

In exemplary embodiments, the head assembly housing 402 may be ring-shaped, or may be oval, square, rectangular or of another shape. For purposes of illustration, but not by way of limitation, a circular shaped housing will be described. The head assembly housing 402 has an interior wall 412 and an exterior wall 414. In exemplary embodiments, an attachment portion 416 is associated with the interior wall 412 and extends at least partially around the circumference of the interior wall 412. In exemplary embodiments, the attachment portion 416 may be a lip or flange that protrudes from the interior wall. The lip may have a groove formed therein. Alternatively, in other exemplary embodiments, the attachment portion 416 can be a groove or channel formed in the interior wall 412.

In exemplary embodiments, the head assembly housing 402 may also have a first connecting member 420 extending from at least a portion of the bottom of the head assembly housing 402. The first connecting member 420 is adapted to connect to a mating second connecting member 422 (for example, see FIGS. 27B and 45) associated with the device main housing 12. In exemplary embodiments, the head assembly housing 402 has a top rim 424 having a ring attachment portion 426, such as a groove or tongue, formed therein. In exemplary embodiments, the head assembly housing exterior wall 414 may have one or more ribs, channels, notches, protuberances or other gripping members 428 formed therein to facilitate gripping of the housing by a user.

Figure 17:
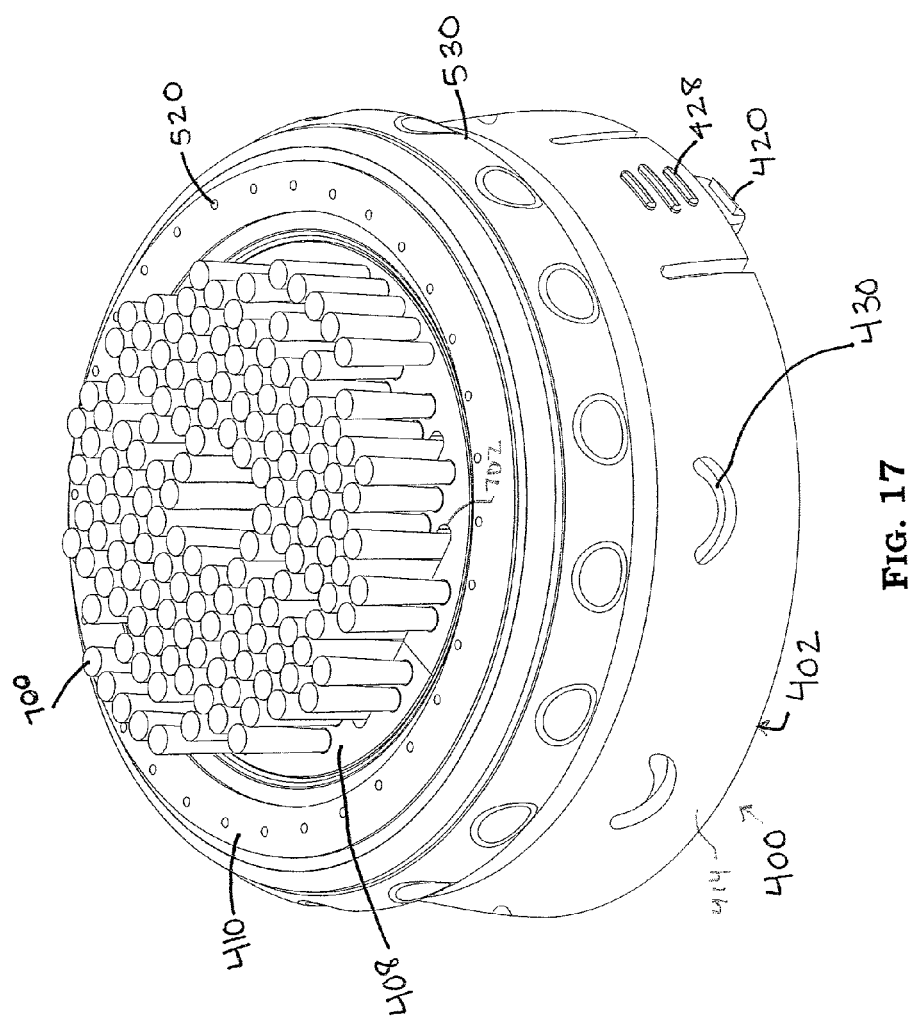
FIG. 17 is a perspective view of a brush head assembly according to one exemplary embodiment.

In exemplary embodiments, such as is shown in FIG. 17, the head assembly housing 402 may include openings 430 to facilitate drainage when cleaning and to permit venting of heat.

In exemplary embodiments, such as is shown in FIGS. 18-19, the first oscillating plate 404 comprises a generally flat plate having a top face 440 and a bottom face 442 and further having a central aperture 444 defined therein. In exemplary embodiments, the first oscillating plate 404 is generally circular, though other shapes are possible. In exemplary embodiments, the surface of each oscillating plate may be configured in other shapes, such as, but not limited to, convex curved, square, rectangular, oval, elliptical, or other regular or irregular shape. The first oscillating plate 404 also has a first boss 446 projecting from the bottom face 442 and proximate to one side. The first boss 446 may have a recessed area 448 defined therein. The first boss 446 can removably receive a pin, such as, for example, the pin 156 from the inner first mounting bracket 120 whereby the ball 158 at the end of the pin 156 is received in the recessed area 448 in the first boss 446.

A second oscillating plate 408 comprises a generally flat plate 450 having a top face 452 and a bottom face 454 and further having a central aperture 456 defined therein. In exemplary embodiments, the second oscillating plate 408 is generally circular, though other shapes are possible. The second oscillating plate 408 also has a boss 458 projecting from the bottom face 454 and proximate to the first side. The boss 458 may have a recessed area 460 defined therein. The boss 458 can removably receive a pin, such as, for example, the pin 188 from the outer second mounting bracket whereby the ball 190 at the end of the pin is received in the recessed area 460 in the boss 458.

In exemplary embodiments, as shown in FIGS. 18-19, the second oscillating plate 408 may be constructed to have a first plate segment 462 and a second plate segment 464 that may be connected. The first plate segment 462 may include at least one, and in exemplary embodiments, a plurality of fingers 466 which are generally parallel to the face of the first oscillating plate. The second plate segment 464 may comprise at least one, and in exemplary embodiments, a plurality of fingers 468. In exemplary embodiments, the first plate segment fingers 466 can interlace with the second plate segment fingers 468 when the two plates are joined together. The first and second plate segments 462, 464 may be locked in place by fastening members 470. In one exemplary embodiment, shown in FIG. 19, the fastening member 470 comprises a pair of tabs or barbs 472 formed in one of the plate segments, and a pair of notches 474 formed in the other plate segments, whereby each tab can matingly snap fit into a notch. In exemplary embodiments, the tabs are on opposing sides of the second oscillating plate 408. Alternatively, the first and second plate segments 462, 464 can be permanently bonded to each other, such as by adhesive, fusing, welding, or the like. In alternative exemplary embodiments, rather than the aforementioned fastening means, the first and second plate segments may be held together by a ring fitted around the edge of both plate segments 462, 464 when fitted together.

Figure 23:
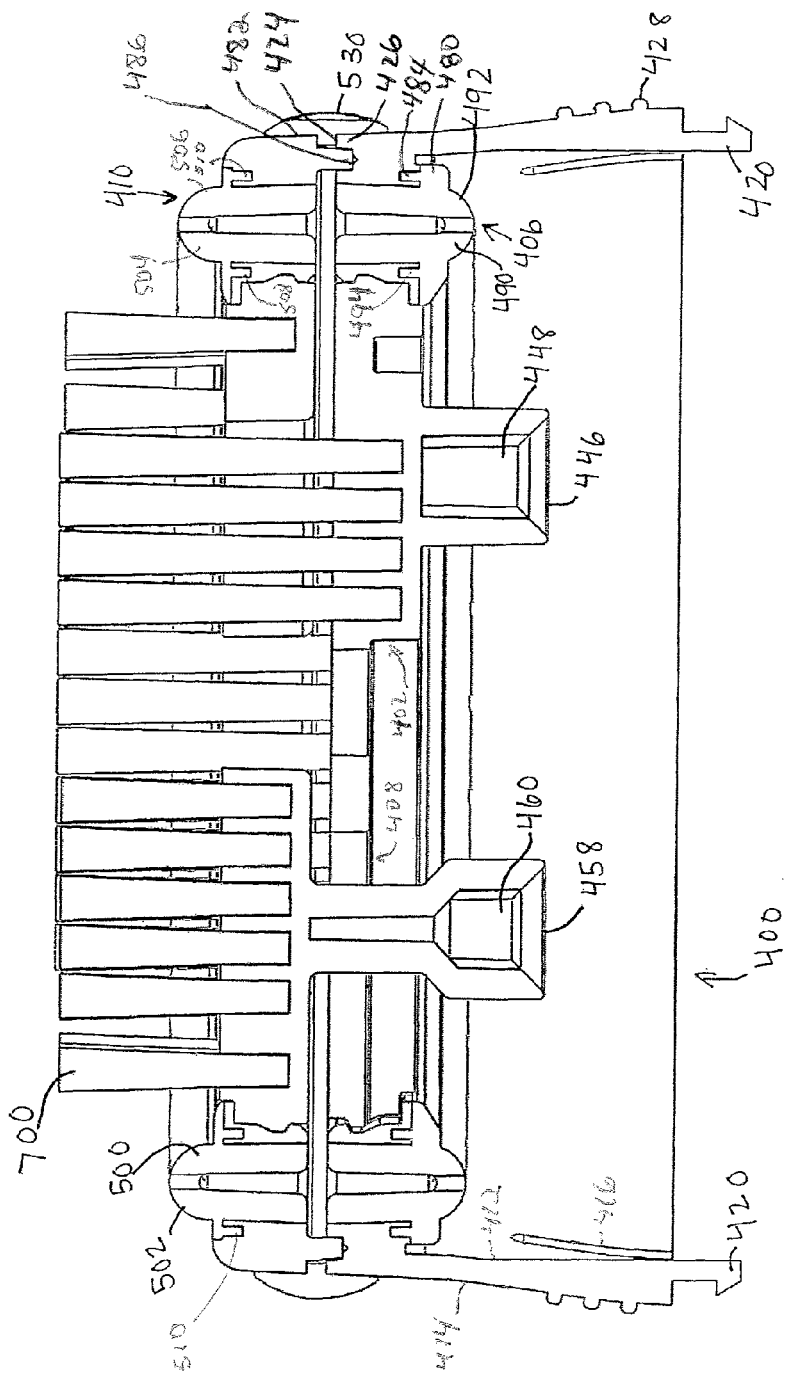
FIG. 23 is a side cutaway view of a brush head assembly according to the exemplary embodiment of FIG. 17.
Figure 24:
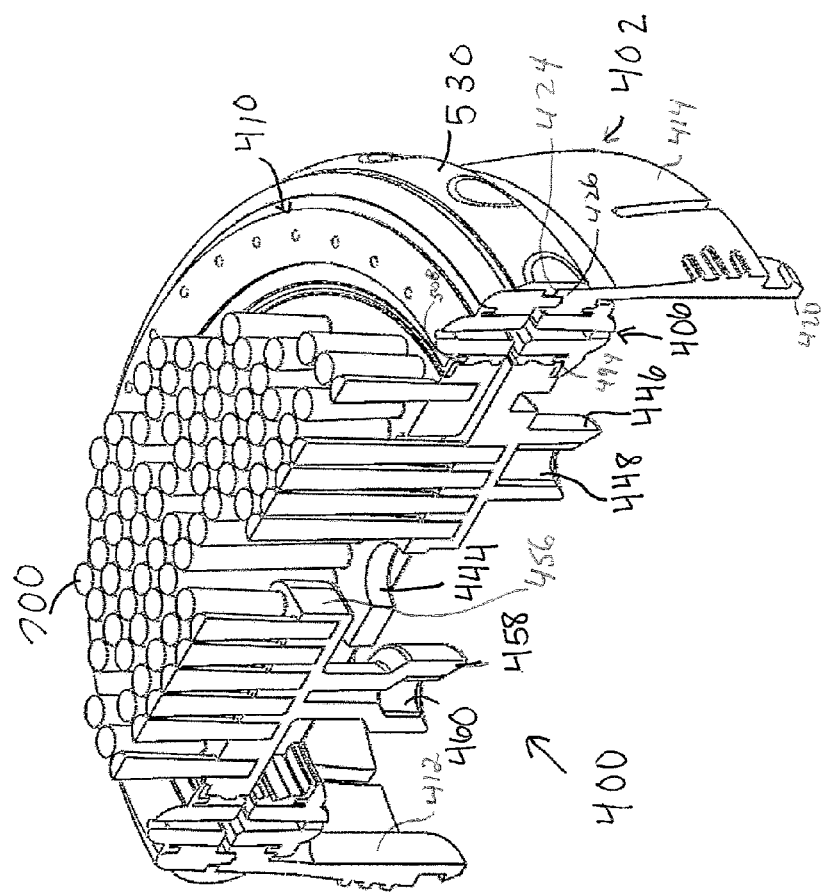
FIG. 24 is a side cutaway perspective view of a brush head assembly according to the exemplary embodiment of FIG. 17.

As shown in an exemplary embodiment in FIG. 23, the first and second oscillating plates may each have a side edge 480, 482 extending around the periphery of each oscillating plate. The first oscillating plate side edge 480 may have a ring attachment portion 484, which may be a tongue or other protrusion or protrusions extending at least partially around the circumference of the oscillating plate. Alternatively, the ring attachment portion may be a groove or at least one recess. The second oscillating plate side edge 482 may have a ring attachment portion 486 similar in construction to that of the first oscillating plate side edge 480.

The first suspension ring 406 may be formed from a material having a degree of flexibility or elasticity, such as, but not limited to, an elastomeric material. In exemplary embodiments, the first suspension ring 406 may comprise or contain a silicone elastomer, such as Silastic® elastomer. The first suspension ring 406 has an interior side 490 and an exterior side 492. In exemplary embodiments, the first suspension ring 406 may have a generally curved or U-shaped cross-section. In exemplary embodiments, the first suspension ring may be constructed to have a cross-section that includes pleats, folds (such as accordion folds), waves, undulations, curves or involutions to increase the cross-sectional length and the flexibility or movement of the ring structure.

The interior side 490 may have an attachment portion 494 formed therein. In exemplary embodiments, the attachment portion 494 may be a protrusion (or protrusions spaced around the periphery), such as a tongue, extending at least partially around the interior side, or, alternatively, the attachment portion 494 may be a recess, such as a groove or channel (or several) extending at least partially around the interior side. The first suspension ring 406 is attached to the inner wall 412 of the head assembly housing 402. In exemplary embodiments, the first suspension ring 406 is co-formed, co-molded with, welded, glued or snap-fitted to, or otherwise associated with the head assembly housing 402.

The second suspension ring 410 may be formed of an inner ring 500 and an outer ring 502 (as shown, for example, in FIG. 23). The inner ring 500 may be formed from a material having a degree of flexibility or elasticity, such as, but not limited to, an elastomeric material. In exemplary embodiments, the inner ring may comprise or contain a silicone elastomer, such as Silastic® elastomer. The inner ring 500 may be formed of the same or a different material from that of the first suspension ring 406. The outer ring 502 may be formed of a material having a higher durometer than the inner ring 500. In exemplary embodiments, the outer ring 502 is formed from a relatively rigid material, such as polymer plastic. In exemplary embodiments, the inner and outer rings 500, 502 are attached to each other, or may be co-formed or co-molded together. Alternatively the inner and outer rings 500, 502 can be connected by welding, gluing, snap fitting or other attachment means known to those skilled in the art.

In exemplary embodiments, the second suspension ring 410 may have a generally curved or inverted U-shaped cross-section. In exemplary embodiments, the second suspension ring 410 may be constructed to have a cross-section that has pleats, folds (such as accordion folds) or involutions to increase the flexibility or movement of the ring structure.

The second suspension ring 410 has an interior side 504 and an exterior side 506. The interior side 504 of the second suspension ring 410 has a plate attachment portion 508 formed therein. In exemplary embodiments, the plate attachment portion 508 may be a protrusion (or protrusions spaced around the periphery), such as a tongue, extending at least partially around the interior side, or, alternatively, the attachment portion 508 may be a recess, such as a groove or channel (or several) extending at least partially around the interior side 504.

The bottom edge of the outer ring 502 may have a housing attachment portion 510 (as shown, for example, in FIG. 23) comprising a tongue or set of protrusions that can mate with the groove or recesses of the ring attachment portion 426 of the top edge of the head assembly housing.

The second suspension ring 410 can be attached to the second oscillating plate 408 in a manner similar to how the first suspension ring 408 is attached to the first oscillating plate 404, namely, by snap-fitting the oscillating plate in the ring.

Figure 25:
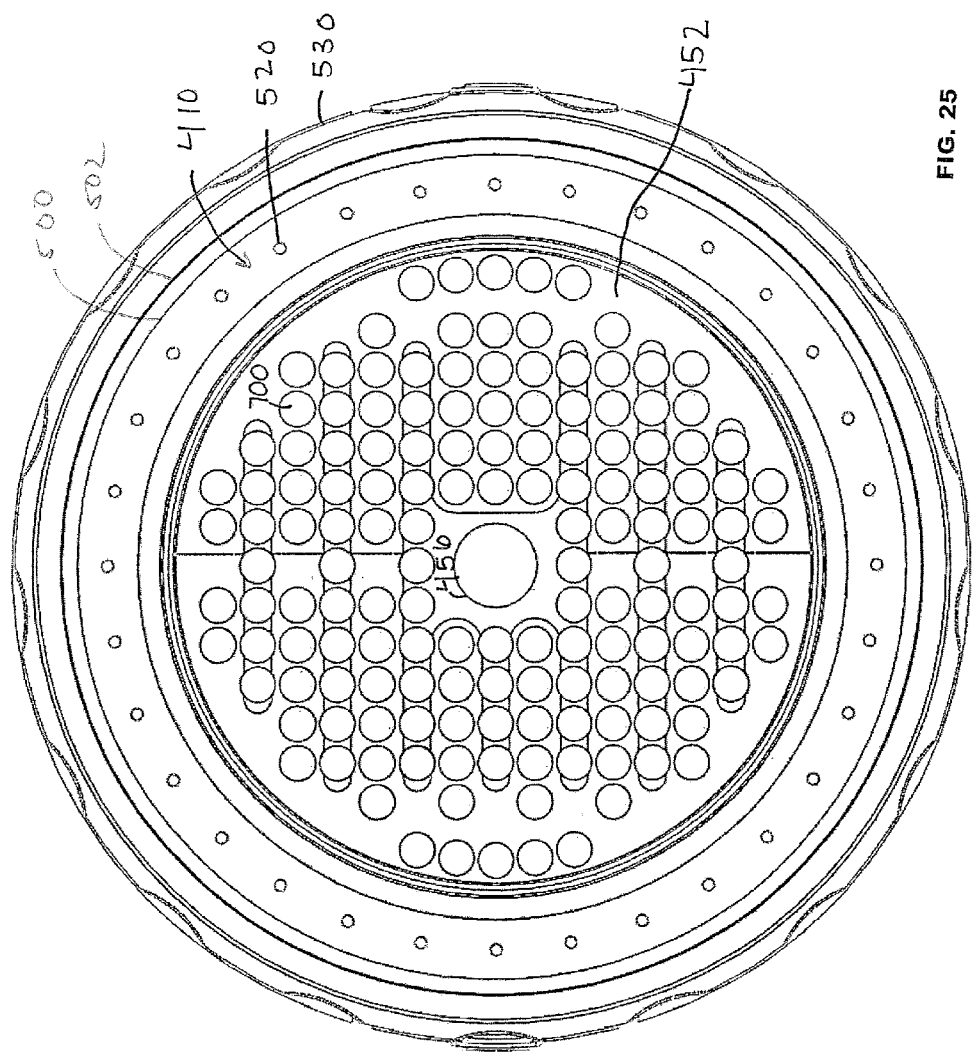
FIG. 25 is a top view of a brush head assembly according to the exemplary embodiment of FIG. 17.

In exemplary embodiments, one or both of the suspension rings 406, 410 may have one or more drainage openings 520 formed therein, as shown in FIG. 25. The openings 520 may be holes, slots or the like.

The brush head assembly 400 is assembled by first snap-fitting the first oscillating plate edge into the first suspension ring 406. The second oscillating plate edge is snap-fitted into the second suspension ring 410. The second suspension ring 410 with the second oscillating plate 408 can then be joined to the housing 402 by connecting the housing attachment portion 510 to the ring attachment portion 484. The joint can be sonically welded, glued or otherwise made a permanent joint.

Optionally, in exemplary embodiments, a retaining band 530 may be used to cover any joint gap between the top edge of the brush head assembly housing and the second suspension ring be stretched slightly and force-fitted over the second suspension ring 410 and the first suspension ring 406. The retaining band 530 may have an annular tongue 532 (as shown, for example, in FIG. 21) that fits in the joint gap. The retaining band 530 may be formed of a material having some degree of elasticity. FIGS. 22-25 show exemplary embodiments of an assembled brush head assembly 400.

In exemplary embodiments, the brush head assembly 400 can be attached to the main housing 12 by snap-fitting or otherwise connecting the housing connecting member to the main housing 12. The first mounting bracket pin 156 fits in the boss of the first oscillating plate 404. Similarly, the mounting bracket pin 188 fits in the boss of the second oscillating plate 408. An exemplary embodiment of an assembled device 10 and brush head assembly 400 (resting in a cradle, as is described in greater detail hereinbelow).

The suspension rings permit movement of the oscillating plates in the X-, Y- and Z-axes due to the elasticity or flexibility of the ring structures, as will be discussed in greater detail hereinbelow.

Figure 26:
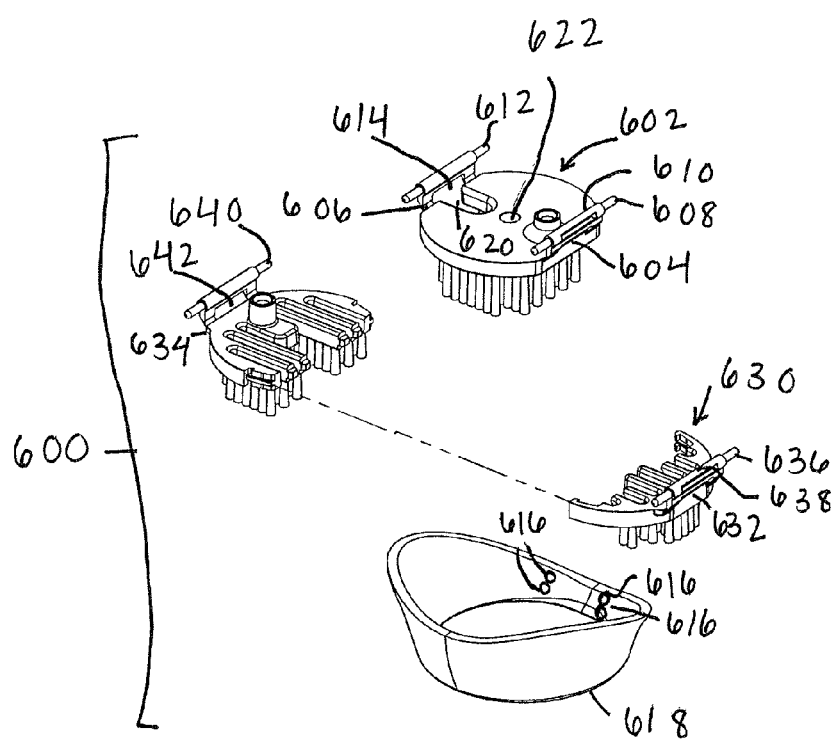
FIG. 26 is an exploded perspective view of first and second oscillating plates according to an alternative exemplary embodiment.

FIG. 26 shows an alternative exemplary embodiment of a brush head assembly 600 and having a first oscillating plate 602 may have a flattened first side 604 proximate to the slot and an opposing flattened second side 606. A first pin 608 is connected to a first side of the first oscillating plate 602 by a first hinge 610. Similarly, a second pin 612 is connected to a second, opposing, side by a second hinge 614. Each hinge 610, 614 is able to flex slightly to permit a degree of movement of the first oscillating plate 602 relative to the hinges. The each end of each hinge 610, 614 can be received within a mating boss 616 foamed in the head assembly housing 618. In exemplary embodiments, the first oscillating plate 602 may have a slot 620 extending from the first side toward a central aperture 622.

A second oscillating plate 630 may have a flattened first side 632 and an opposing flattened second side 634. A first pin 636 is connected to the first side of the second oscillating plate by a first hinge 638. Similarly, a second pin 640 is connected to the opposing second side of the second oscillating plate 630 by a second hinge 642. Each hinge is able to flex slightly to permit a degree of movement of the second oscillating plate 630 relative to the hinges. The each end of each hinge can be received within a mating boss 616 formed in the head assembly housing 618. In exemplary embodiments, the hinges 610, 614 of the first oscillating plate 602 and the hinges 638, 642 of the second oscillating plate 630 may be generally parallel.

In exemplary embodiments of the brush head assembly 400 that include first and second oscillating plates, such as plates 404, 408, the first oscillating plate 404 has a plurality of protrusions 700 extending from the bottom face. In exemplary embodiments, the base of each protrusion 700 may be fitted within a recess formed in the bottom face of the oscillating plate.

In exemplary embodiments, the protrusion 700 can be a tuft. In exemplary embodiments, the tuft may be formed of a plurality of bristles, the bristles being either all the same length or may have bristles of various lengths. The bristles may be made of natural or synthetic materials and the stiffness can be adjusted by the selection of the material, flexibility, thickness, length, and other properties. In exemplary embodiments, the bristles may be arranged in a uniform density or one or more tufts may have a distinct bristle density such that the overall density across the plate varies. The bristles may be straight, curled, spiral, twisted or have other shapes.

In exemplary embodiments, the protrusion 700 may have a solid structure. In exemplary embodiments, a solid protrusion can be formed of a material having a degree of flexibility, such as, but not limited to, silicone elastomer, or other elastomer, metal wire, plastic rods or the like. In exemplary embodiments, a solid protrusion 700 may be molded into recesses in the bottom face 442 of the first oscillating plate, or can be inserted into the recesses after formation of the plate. In exemplary embodiments, the protrusions 700 can be co-formed or co-molded as part of the surface of one or both of the oscillating plates. In exemplary embodiments, the distal end of the solid protrusion 700 may be flat, beveled, rounded, conical, tapered, pointed, ball-ended, convex curved or the like. Alternatively, the protrusion may have a concave cup at the distal end. The distal end (and/or portions of the sides) of the protrusion 700 may be smooth or textured or may have ridges, bumps, fingers, divots, recesses, or other extensions or involutions. In exemplary embodiments, the distal end of the protrusion 700 may have a concave recess. In exemplary embodiments, the solid protrusion may have a recessed well formed therein, the well capable of receiving and temporarily retaining or delivering fluid. In exemplary embodiments, the protrusions 700 can be of a single type or can be of two or more different types. For example, some protrusions 700 may be tufts of bristles while others can be solid protrusions. Different materials may be used, such as, but not limited to, materials with different durometer. In exemplary embodiments, the protrusions 700 are arranged in rows.

The second oscillating plate 408 may have protrusions 700 selected from the group of protrusions 700 described hereinabove with respect to the first oscillating plate 404. Similarly, the protrusions 700 extend from the bottom face 454 of the second oscillating plate 408 and may be fitted within recesses in the bottom face or formed with the plate similar to as described hereinabove. The protrusions 700 in the second oscillating plate 408 may be the same as those used in the first oscillating plate 404, or may be different. The protrusions 700 in the second oscillating plate 408 may have the same length as the protrusions 700 in the first oscillating plate 404, or may be of a different length. In exemplary embodiments, the protrusions 700 in the first oscillating plate 404 are longer than those in the second oscillating plate 408 so that when the two plates are aligned all the distal ends of the protrusions 700 in both oscillating plates are generally co-planar. In exemplary embodiments, the protrusions 700 in the second oscillating plate 408 can be arranged in rows. In exemplary embodiments, there may be elongated openings or slots 702 between the rows of protrusions (as shown, for example, in FIGS. 19 and 20). In exemplary embodiments, the rows of protrusions 700 in the first oscillating plate 404 can be fitted in and at least partially through the elongated openings 702, resulting in the rows of protrusions from both first and second oscillating plates being interspaced to form a brush head.

In exemplary embodiments, a wear indicator material may be associated with the protrusions, such as by being impregnated, co-formed or coated. In exemplary embodiments, the protrusions may have medicinal, therapeutic, cosmetic, lubricant or other material coated on or impregnated in the protrusion composition, which material can be gradually released onto the skin or other surface being treated during contact by the protrusions.

In exemplary embodiments, rather than the oscillating plates having protrusions, the second oscillating plate 408 (such as an exemplary embodiment where just one oscillating plate is employed, as described in greater detail herein) may have a soft cover or surface, such as, but not limited to, felt or other fabric, foam, synthetic material, or the like. Such material may be attached to the oscillating plate bottom face as a cover. In exemplary embodiments, the oscillating plate may have a hard surface or cover, such as but not limited to, ceramic, sandpaper-like material (i.e., a granular or particulate material, such as, but not limited to minerals, silica, sintered metal, textured metal or plastic (e.g., sandblasted or bead blasted or the like) adhered to or formed as part of a substrate), wire bristles, buffing material, or the like. In exemplary embodiments, the protrusions 700 may comprise or incorporate optical fibers that can transmit light energy.

Figure 27A:
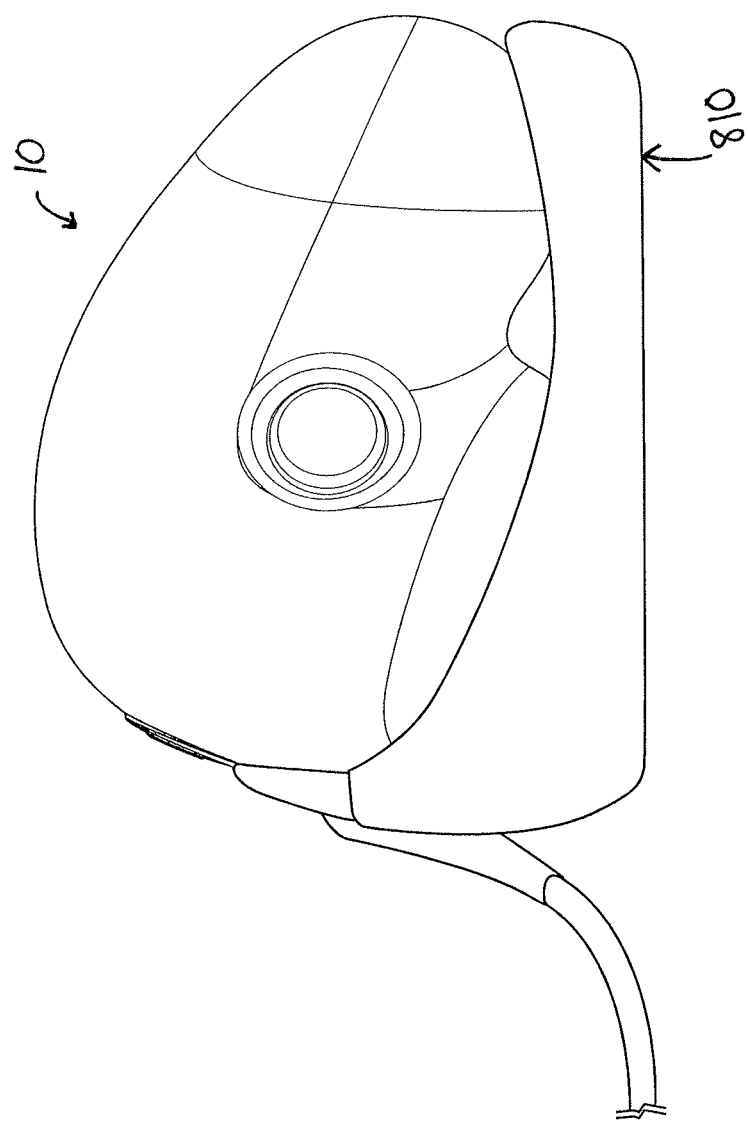
FIG. 27A is a side schematic view of a device resting in a recharging cradle according to one exemplary embodiment.

In exemplary embodiments, the device 10 further includes a power supply (referred to generally as 800). In exemplary embodiments, as shown in FIGS. 1 and 27A, the power supply 800 may be a rechargeable or disposable battery 802 contained in the main housing 12. In exemplary embodiments, the power supply 800 may be provided by an electrical connection between the motor and an external power source, such as an AC outlet. In exemplary embodiments, the power supply may be provided by a USB or similar connection to a device (such as, but not limited to, a personal computer or other computing device) or a battery, solar, capacitor, fuel cell or other power source.

In exemplary embodiments, an induction charging system may be used in which one induction coil 804 (not shown) is disposed inside the main housing 12 and a second induction coil (not shown) is external to the device and connected with a power supply. FIGS. 4 and 27A illustrates a portion of a charging system showing an induction coil 804 and battery 802 incorporated in a main housing. In exemplary embodiments, the charging system may include a cord that plugs into the device at a charging port and is also connected to a power supply.

In exemplary embodiments, a cradle 810 is provided that may house the external induction coil and a connection to an AC power source, an onboard battery, or connection to another type of power source. In exemplary embodiments, as shown in FIG. 27A, the cradle 810 is shaped to hold the device 10. In exemplary embodiments, the cradle 810 may be used to store or transport the device.

Figure 27B:
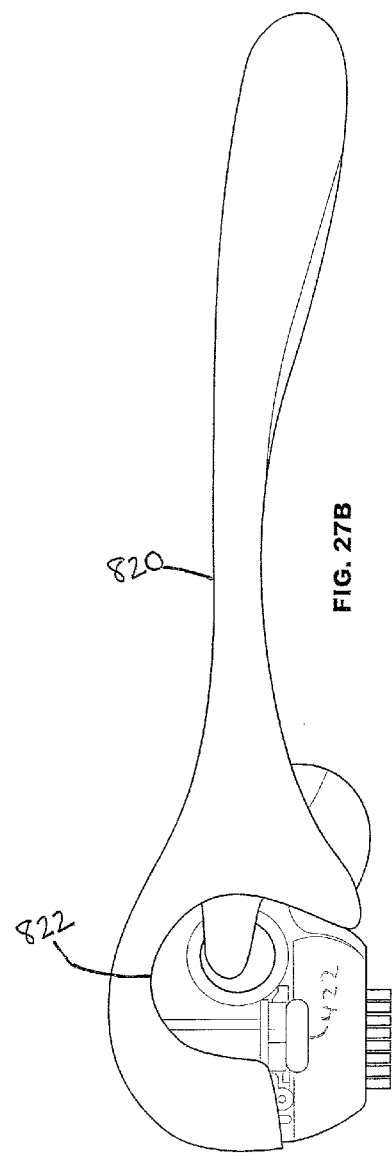
FIG. 27B is a side view of a device and a detachable handle according to one exemplary embodiment.
Figure 27C:
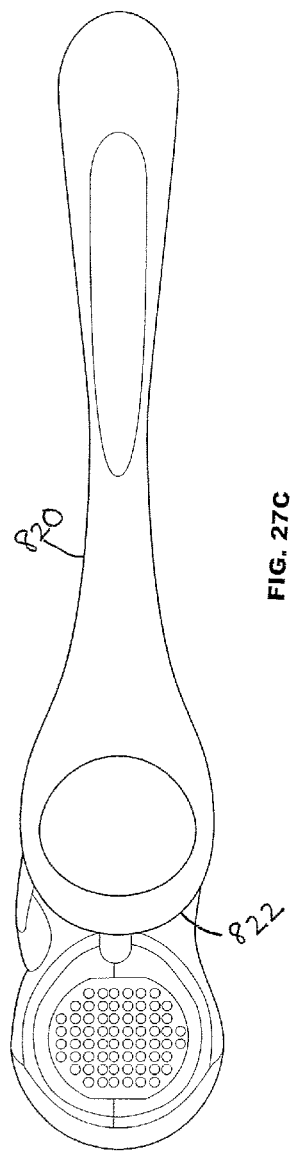
FIG. 27C is a front view of a device and a detachable handle according to the exemplary embodiment of FIG. 27B.

In exemplary embodiments, as shown in FIGS. 27B, C, the device 10 may at least partially fit within a handle 820 to extend the reach of a user. The handle 820 may include a recessed area 822 or pocket in which the device may be removably inserted.

Figure 28:
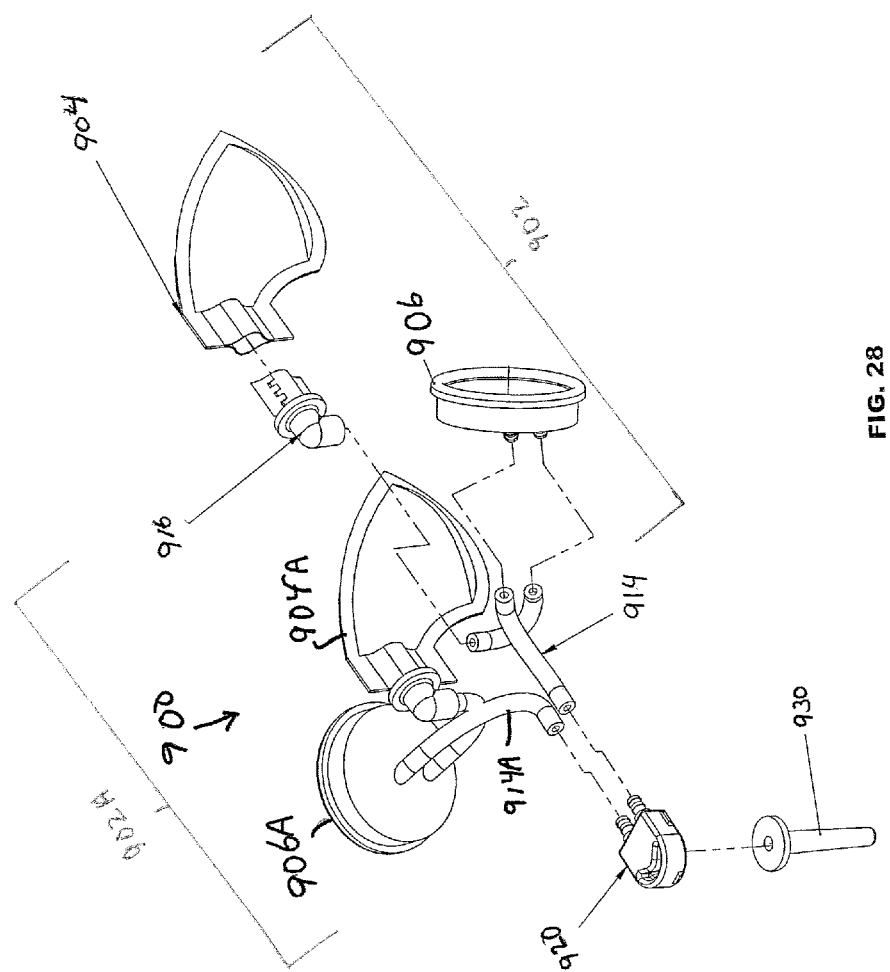
FIG. 28 is a schematic perspective view of a fluid delivery system according to one exemplary embodiment.

In exemplary embodiments, for example as shown in FIG. 28, the device 10 also includes a fluid delivery system 900 incorporating at least one fluid delivery module 902 that can convey a measured amount of a fluid from a reservoir 904 through the oscillating plates and to a surface, such as skin. In exemplary embodiments, the fluid delivery system 900 can be used in conjunction with the brush head assembly 400 or other head assemblies (as further described hereinbelow). The fluid can be a fluid, gel, semi-fluid, suspension, colloidal mixture or other flowable material. For the purposes of illustration only, the term "fluid" will be used, but is intended to include any of the foregoing material. In certain exemplary embodiments, a gas or aerosolized fluid may be deliverable.

In exemplary embodiments, the fluid delivery system 900 includes first fluid delivery module 902 having a fluid reservoir 904, a fluid delivery mechanism 906, such as, but not limited to, a pump or other means (for example, but not as a limitation, by pushing or pulling) for urging fluid from the reservoir 904, and at least one tube 914 or conduit, channel, path or the like for conveying a fluid from the reservoir 904 to a dispensing port 910. One exemplary embodiment of a fluid delivery system is shown in FIG. 28, which comprises a pair of fluid delivery modules 902, 902A disposed in the main housing 12 in generally mirrored configurations. The reservoir 904 can be refillable, or it can be replaceable. A user can access the reservoir 904 by opening a panel, door, flap or other access area 912 in the main housing, as shown in FIG. 1. In exemplary embodiments, the fluid delivery reservoir 904 may be a self-contained assembly, such as a cartridge, that can be removably attached to or otherwise associated with the main housing 12 such that the reservoir can be replaced when empty.

One or more tubes 914 or other conduits is associated with the reservoir 904. The tube 914 may be flexible. In exemplary embodiments, an adapter 916 connects the fluid reservoir and the tube. The delivery mechanism 906 is connected by a tube 914 to the reservoir and to the dispensing port 910.

In exemplary embodiments, a second fluid delivery module 902A is contained inside the main housing 12. The second fluid delivery module 902A may have the same components and arrangement as the first fluid delivery module 902. Similar components are labeled to correspond to the components of the first fluid delivery module, but followed by the letter "A" for differentiation. In exemplary embodiments, a single dispensing port 910, such as that shown in FIG. 28, can be used with both first and second fluid delivery modules 902, 902A, the outlet tubes 914, 914A being connected to a manifold 920 which in turn is connected to the dispensing port 910. A second delivery mechanism 906A may be incorporated, or, alternatively, fluid may be delivered from the reservoirs 904, 904A by a single delivery mechanism. In exemplary embodiments, the combined fluid output delivered by both delivery mechanisms 906, 906A combines in the manifold 920 and is delivered as a combined stream to the dispensing port 910.

Figure 30:
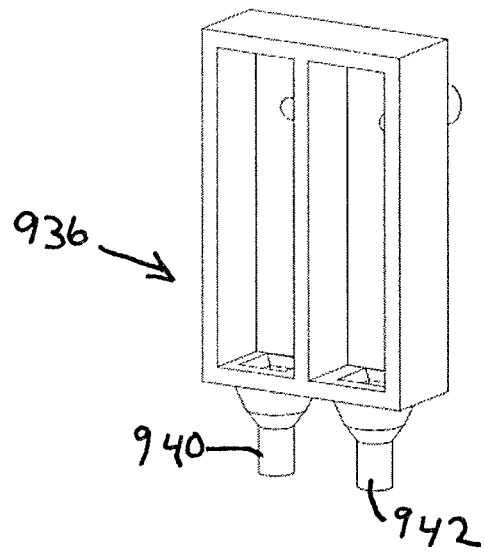
FIG. 30 is a schematic view of a detail of the delivery port according to one exemplary embodiment showing a manifold and two nozzles.
Figure 29:
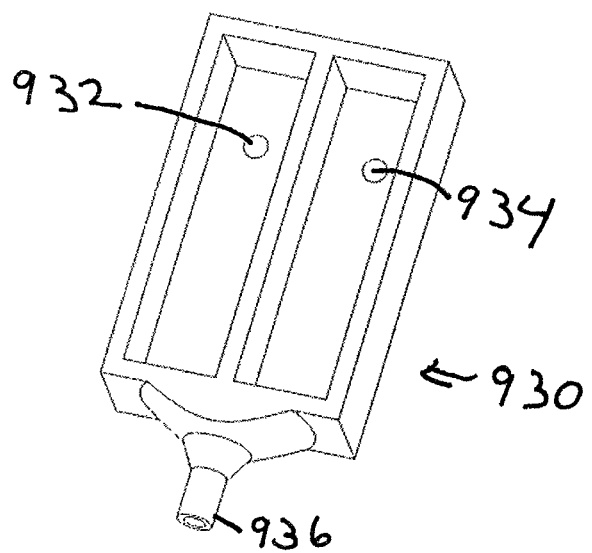
FIG. 29 is a schematic view of a detail of the delivery port according to a second exemplary embodiment showing a manifold and a single nozzle.

In exemplary embodiments, a dispensing port 930, such as one shown in FIG. 29, may have two openings 932, 934, a first opening conducting fluid from the first fluid delivery module, and a second opening conducting fluid from the second fluid delivery module. The fluids are kept separate until they exit the dispensing port 930. Alternatively, as shown in FIG. 30, a dispensing port 936 having two dispensing nozzles 940, 942 can be utilized, each port conducting fluid from one of the fluid delivery modules 902, 902A.

In exemplary embodiments, as shown in FIG. 4, the dispensing port 910 is positioned to have a nozzle portion 946 passing through the central aperture 444 in the first oscillating plate 404 and the central aperture 456 of the second oscillating plate 408 so as to dispense fluid between the protrusions 700. In exemplary embodiments, the nozzle portion 946 can be configured to be shorter than the protrusions so that the nozzle is not felt by a user should the protrusions be bent during use.

Figure 31:
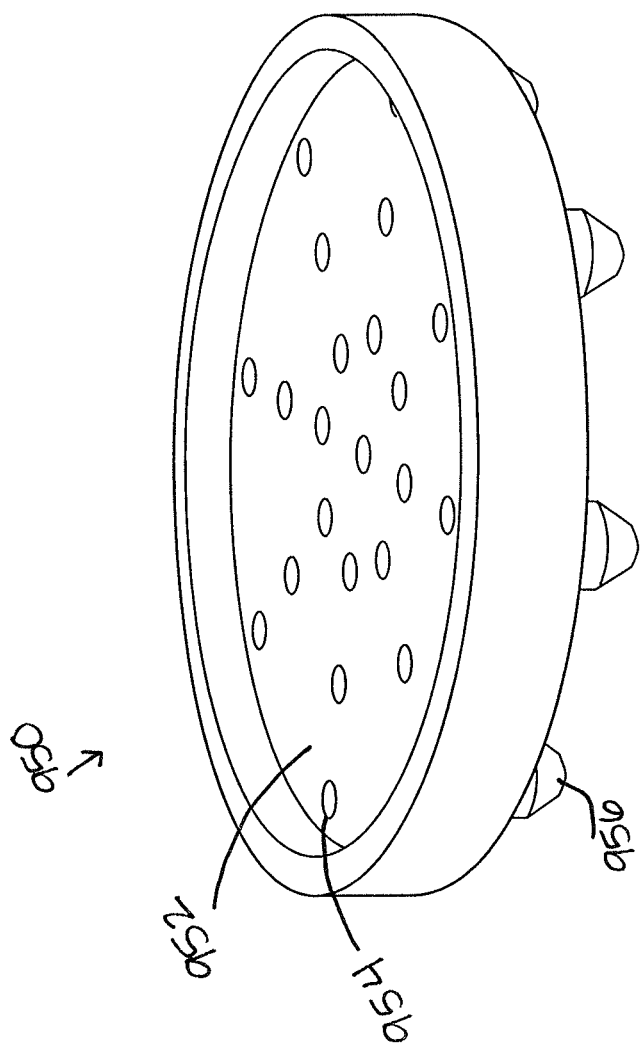
FIG. 31 is a schematic view of a detail of the delivery port according to one exemplary embodiment showing a plate-like manifold with a plurality of nozzles.
Figure 32:
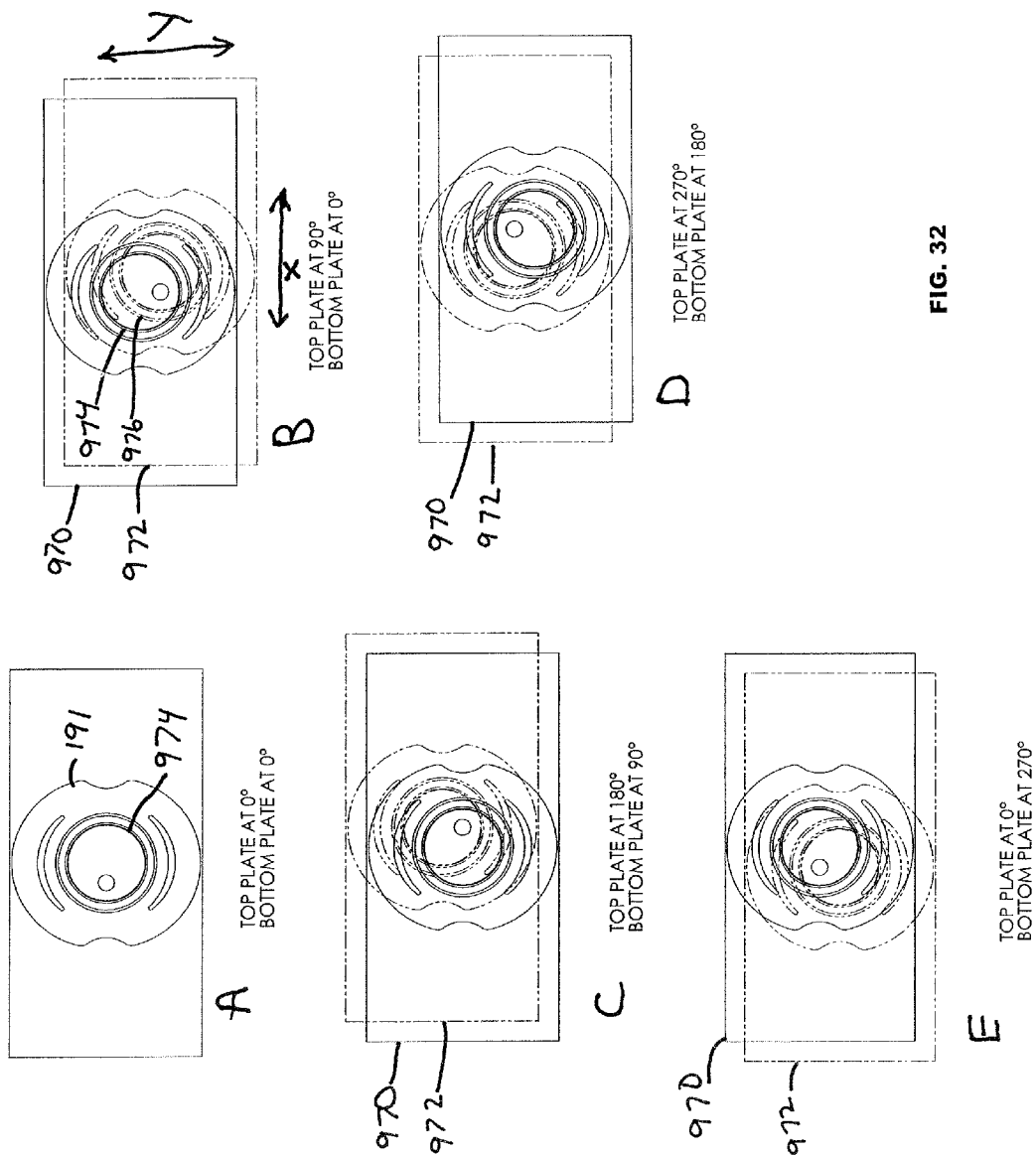
FIG. 32A-E are bottom schematic views of a detail showing the relative oscillating movement of two mounting plates at different positions in an elliptical path, and also shows a grommet and offset axis cam lobe, according to one exemplary embodiment.

FIG. 31 shows an exemplary embodiment of a manifold 950 (shown with a top removed) having a plate 952 plurality of openings 954 and a plurality of nozzles 956 to deliver fluid simultaneously at different places at least partially across the overall surface formed by the protrusions. The manifold 950 may be associated with one of the oscillating plates.

In exemplary embodiments, fluid can be delivered before, during or after application of the device 10 to the surface. In exemplary embodiments, the fluid may have a component that is activatable upon exposure to light, movement, friction, heat or other activation stimulus.

Figure 20:
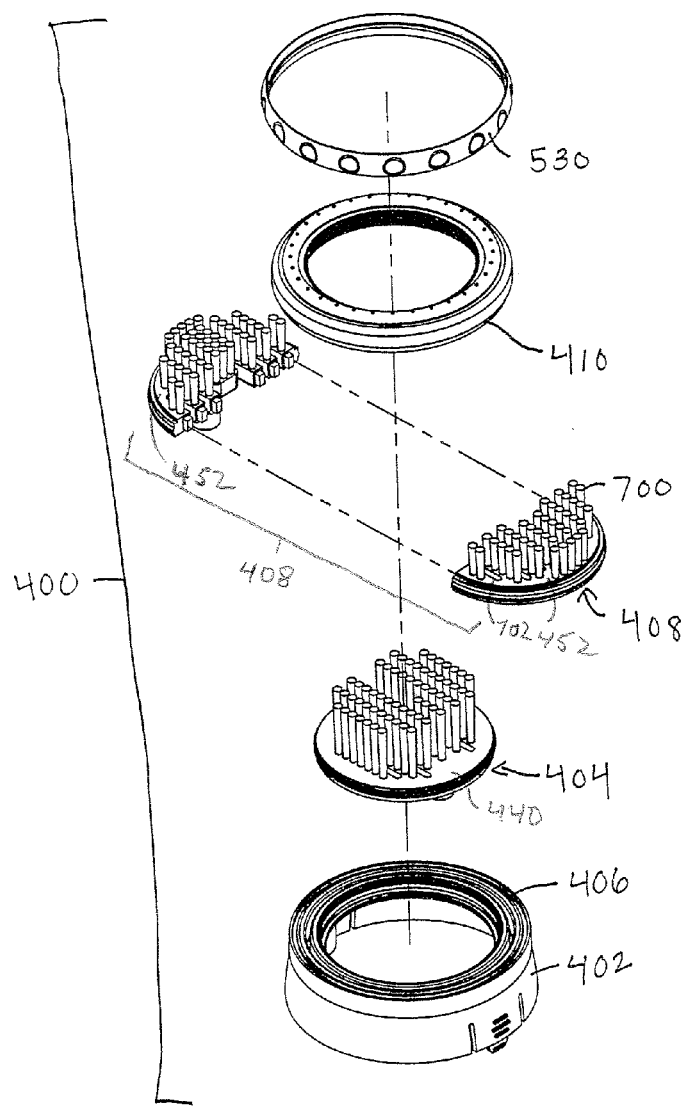
FIG. 20 is a schematic exploded top perspective view of a brush head assembly according to the exemplary embodiment of FIG. 17.
Figure 21:
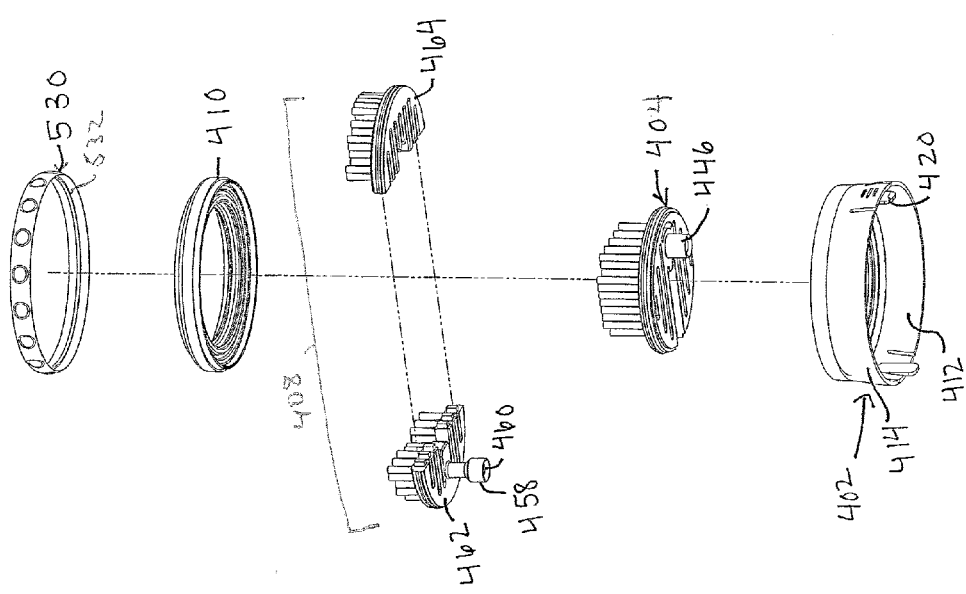
FIG. 21 is a schematic exploded bottom perspective view of a brush head assembly according to the exemplary embodiment of FIG. 17.

A feature of exemplary embodiments of the present device is the unique mechanical motion of the oscillating plates. For illustrative purposes only, the exemplary embodiments in which the oscillating plate assembly comprises first and second oscillating plates (for example, as shown in FIG. 20) will be described. In exemplary embodiments where the first and second oscillating plates are generally flat disk-shaped plates, when the motor is activated, the shaft rotates, causing the cam lobes to rotate. As the cam lobes rotate, the eccentric motion is transmitted to the inner and outer mounting brackets. In exemplary embodiments, the motion of the cam lobes may be transmitted to the mounting brackets via the grommet 191 in the central aperture of each base plate.

FIGS. 32A-E shows views of various relative positions of the first and second mounting bracket base plates and a grommet and cam as the base plates progress around one 360 degree elliptical path. FIG. 32A shows both the second mounting bracket base plate (noted in the drawings and referred to in the present discussion of the relative plate motion as "top plate" 970 in solid line in the various views) and the first mounting bracket base plate (noted in the drawings and referred to in the present discussion of the relative plate motion as "bottom plate" 972 in dashed line in the various views), as well as the top plate 970 cam lobe 974 and the bottom plate 972 cam lobe 976 at the 0° initial position. FIG. 32B shows the top plate (in solid line) at 90° and the bottom plate still at 0°. FIG. 32C shows the top plate at 180° and the bottom plate now at 90°. The bottom plate essentially follows the top plate through the elliptical path, lagging by 90°. FIG. 32D shows the top plate at 270° and the bottom plate at 180°. FIG. 32E shows the top plate back at 0° and the bottom plate at 270°. The figures also show the movement of the cam lobe of the top and bottom base plates at each rotates.

Movement of the mounting bracket base plates is in the direction indicated in FIG. 32B as the X-axis and also in the Y-axis, thereby defining an elliptical movement path. The elliptical movement of the mounting brackets is transmitted to the pins. The inner mounting plate pin (which has its distal end associated with the boss on the first oscillating plate) transmits elliptical movement to the first oscillating plate. The outer mounting plate pin (which has its distal end associated with the boss on the second oscillating plate) transmits elliptical movement to the second oscillating plate. The elliptical movement of the first oscillating plate is offset from the elliptical movement of the second oscillating plate. In exemplary embodiments, each oscillating plate moves in only one direction, such as counterclockwise, and does not move in the reverse direction. Alternatively, each oscillating plate may move in just the clockwise direction.

Figure 33:
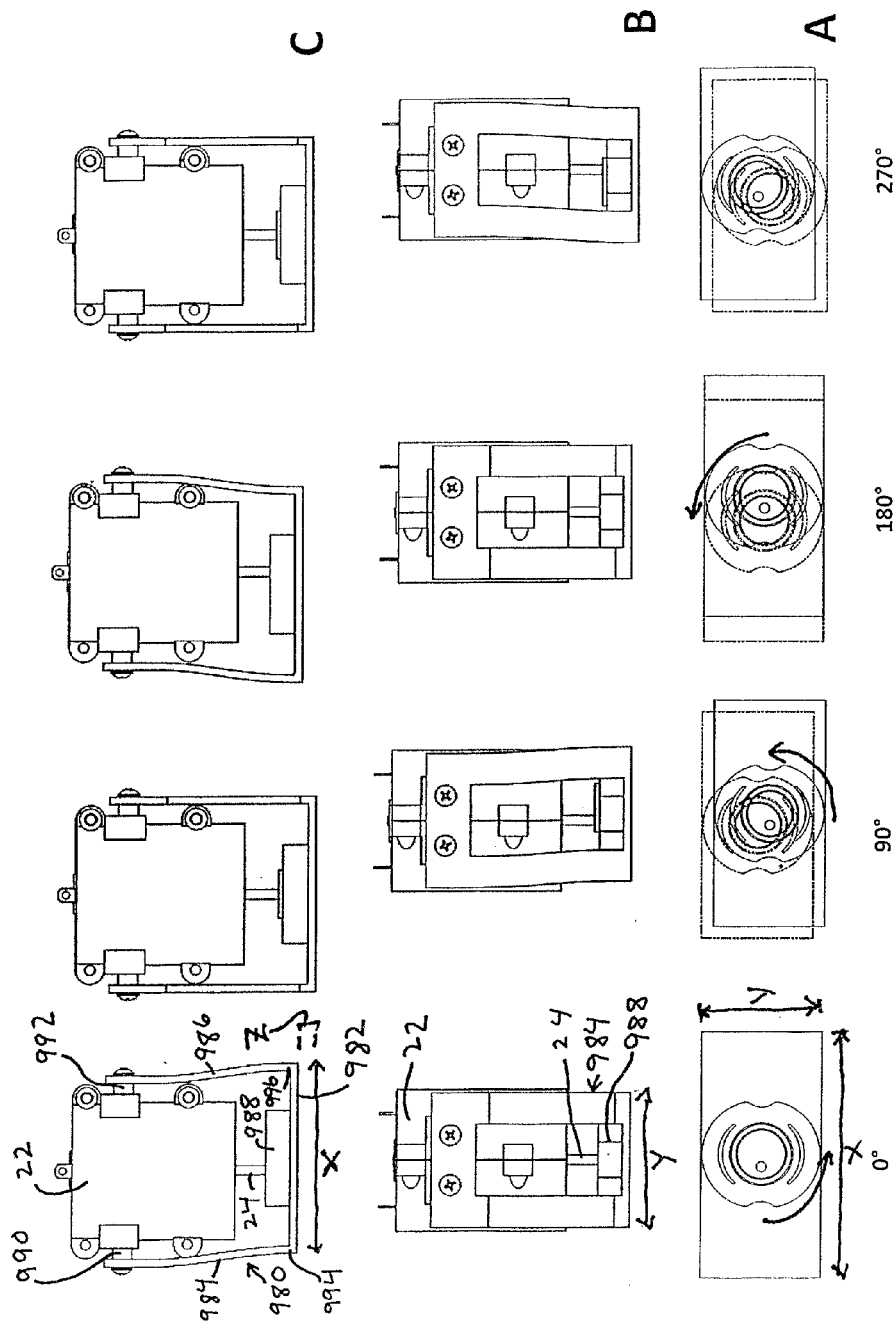
FIG. 33 is a set of three rows of schematic views of the movement through a cam rotation cycle of 0, 90, 180 and 270 degrees and showing the movement of the mounting plate (bottom views, Row A), right side views of the mounting bracket (Row B), and front views of the mounting plate and motor (Row C).

FIG. 33 shows various aspects of a single representative mounting bracket 980 (in this embodiment shown associated with a motor housing 26 that contains a motor 22 and showing a shaft 24) having base plate 982, a first arm 984 and second arm 986 in various stages of movement. Row A shows the movement of the base plate 982 (as shown in a bottom view) in each of 0, 90, 180 and 270 degrees positions of a counterclockwise rotation of a cam 988 (shown in this embodiment for purposes of simplification of the explanation of movement as having just a single offset cam lobe, and which is shown only partially fitted in the base plate central aperture). The off-axis rotation of the cam 988 (or other elliptical motion creating mechanism) causes the grommet 191 and the mounting bracket base plate 982 to move in an elliptical path with X- and Y-axis movement of the base plate 982. The 90 degree position shows movement in the X- and Y-axes down and to the right (relative to the 0 degree initial position). The 180 degree position shows movement in the X-axis to the left. The 270 degree position shows movement in the X- and Y-axes up and to the right.

The arms 984, 986 may flex in the Y-axis direction as shown in Row B. The arms 984, 986 may flex in the X-axis direction, as shown in Row C. In exemplary embodiments, the arms 984, 986 may pivot about the connecting members 990, 992 to provide Y-axis movement to the arms and 984, 986 the base plate 982.

In exemplary embodiments, the mounting bracket base plate 982 also may move in the Z-axis due to the pivoting aspect of the movement of the mounting bracket arms 984, 986 which pivot at the point of association with the motor or the motor housing. The Z-axis may be generally defined as an axis orthogonal to both the X-axis and Y-axis. In one aspect, as shown in FIG. 33 (the left-most figure in row C) the structure of the mounting bracket 980 and the connecting members 990, 992 form a parallelogram linkage in which the pairs of pivot points may be the male and female connecting portions of each connecting member as one pair, and the edges 994, 996 of the base plate (by flexion) as the other pair. The pivoting motion of an arm about a pair of fixed points (the points of attachment to the motor housing) creates the arc of movement the arms, thereby causing the base plate 982 to rise and fall (with respect to the (stationary) motor) and providing the Z-axis movement component.

In exemplary embodiments, the path of the elliptical movement may be 0.010 inches (0.254 millimeters) in the X-axis and 0.005 inches (0.127 millimeters) in the Y-axis. It is to be understood that amount of axial movement may be changed by changing aspects of various components of the device, such as, but not limited to, the length, diameter, stiffness or other aspect of the protrusions, the diameter of the cam lobes, the amount of offset of the cam lobes, or the like. In exemplary embodiments, the amount of Z-axis movement may be 0.0002 inches (0.00508 millimeters).

The eccentricity and size of the elliptical movement can be adjusted by adjusting, for example, the dimensions of the cam lobes, the amount of axial offset of the cam lobes, the stiffness of the grommet, the axial stiffness of the mounting brackets plate arms, motor speed or other aspects. The amount of Z-axis movement can be adjusted by changing the length of the mounting bracket arms. Shorter arms will create more Z-axis movement.

A feature of the construction of exemplary embodiments of the present device is that the elliptical path movement of the oscillating plates and the ability to control the amount of X- and Y-axis movement independently, can provide more even, controllable movement of the protrusions. Additionally, the movement of each protrusion in each oscillating plate is the same. In contrast, conventional mechanisms that use rotation have an arc, the protrusions near the axial center of the plate or other rotating surface have a different circumscribed path than the protrusions near the edge of the plate since the latter are farther away from the axis of rotation. The farther the protrusion is from the axial center of rotation, the greater the arc.

Another feature of exemplary embodiments of the presently disclosed device is that biplanar elliptical movement is provided, namely, the first oscillating plate is in one plane and the second oscillating plate is in a second, different, plane. A further feature of exemplary embodiments of the presently disclosed device is that the brush head assembly construction and movement allows for each individual tuft to elliptically oscillate (X- and Y-axis) and rise/fall (Z-axis), so that the skin is massaged and cleansed twice with each pass of the brush plate protrusions.

In exemplary embodiments, the motion of the oscillating plates provides vibrational movement to the device, which can be transmitted to the skin or other surface. Vibration of the skin may be useful in enhancing certain treatments, such as, but not limited to, increasing light penetration in light treatment, as described further hereinbelow.

In exemplary embodiments, the presently disclosed device provides a handheld apparatus for delivering mechanical energy to a surface, such as, but not limited to, skin, scalp, nails and the like. The brush head assembly can be used to clean skin, scalp or otherwise treat a surface. It can also be used to increase blood circulation to the dermis layer where age-related components such as collagen reside. The brush head assembly may be useful as an aid in diminishing the appearance of roughness scaling or hyperkeratosis of the skin, superficial hyperpigmentation and photo-damage. It also may be useful as an aid in diminishing fine lines, wrinkles, acne, and shallow scars.

Figure 34:
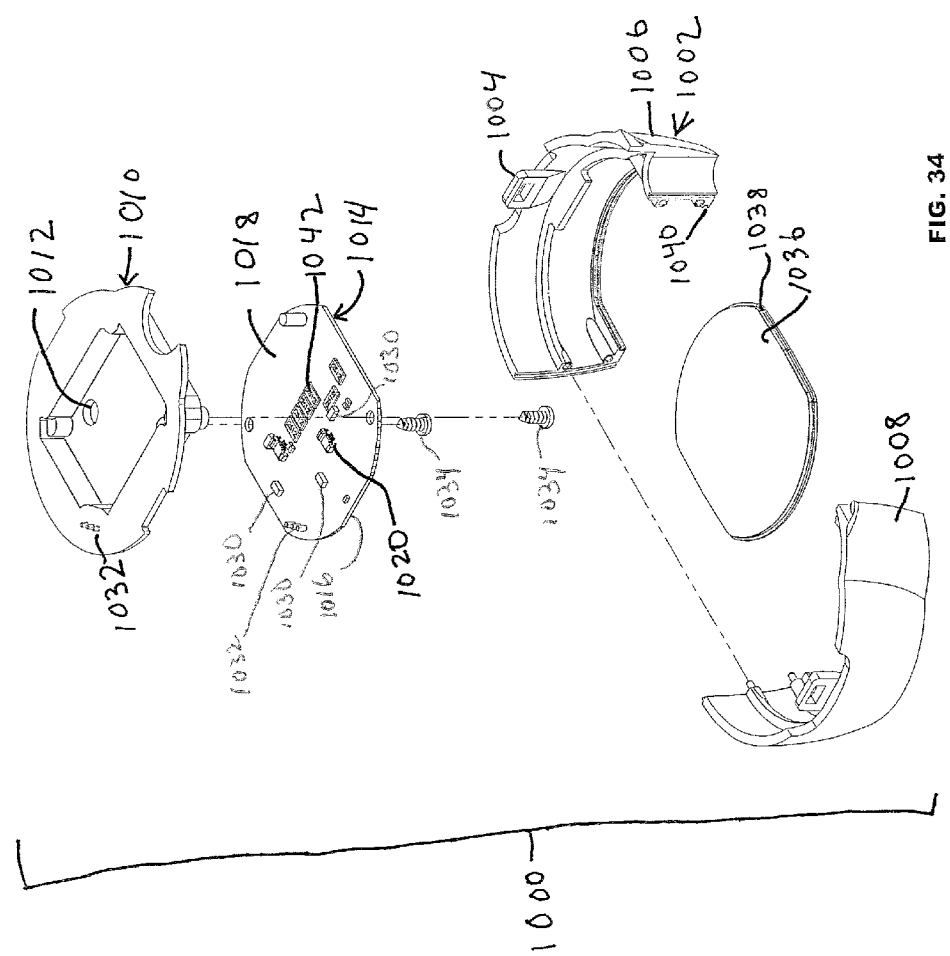
FIG. 34 is an exploded perspective view of a light head assembly according to one exemplary embodiment.

FIG. 34 shows an exemplary embodiment of a light-emitting head assembly 1000. For the purposes of the present disclosure, "light" is intended to include visible, ultraviolet, infrared and other portions of the electromagnetic spectrum, as appropriate for the given use, and also includes laser-generated energy, as well as fluorescent, dichroic and other types of light. In exemplary embodiments, the light-emitting head assembly 1000 includes a housing 1002 which may include at least one fastening member 1004, such as a clip or the like, for detachable connecting to the main housing of the device. In exemplary embodiments, the light-emitting head assembly housing 1002 may comprise two portions 1006, 1008 that can be joined together. In one exemplary embodiment, the light-emitting head assembly 1000 may further include a connection plate 1010 having a first opening 1012 that can accommodate the pin 156 from the inner first mounting bracket 120. In exemplary embodiments, the light-emitting head assembly 1000 may further include a circuit board 1014 having a bottom face 1016 and top face 1018. The circuit board may include a microcontroller or microprocessor 1020 that is in electrical communication with one or more light emitting devices 1030. The light emitting device 1030 may be an LED, incandescent lamp, infrared light-emitting device, optical fiber or bundle of fibers that can convey laser or other light, or the like. In exemplary embodiments, different types of light emitting devices can be utilized on the circuit board 1014. The light-emitting head assembly 1000 may have a first electrical connection member 1032 to electrically connect the head with the microcontroller 54 in the main housing. In exemplary embodiments, the connection member may be one or more electrical contacts that are disposed in the connecting plate 1010 and a set of complementary contact or contacts 1032 disposed in the main housing 1002. In exemplary embodiments, the microcontroller 1020 can be controlled by the microcontroller 54 and the actuation device can include controls for activating and controlling the various light emitting devices. Alternatively, the light-emitting head assembly housing may include an actuation mechanism 50 in communication with the light-emitting head microcontroller 1020. In exemplary embodiments, the controls may be on the light-emitting head assembly housing. The circuit board 1014 may be attached to the connection plate 1010 by one or more fastening member 1034.

In exemplary embodiments, the light-emitting head assembly 1000 may further include a lens 1036. In exemplary embodiments, the lens 1036 may have a tongue 1038 or groove extending at least partially around the perimeter of the lens 1036, and the housing 1002 may have a mating groove 1040 or tongue formed in at least a portion of the housing 1002 so that the tongue 1038 fits in the groove 1040 to maintain the lens 1036 in position. Alternatively, the lens 1036 may be attached to the housing 1002 by welding, gluing, snap fitting or other fastening means. The lens 1036 can be clear or translucent. The lens 1036 may have a diffraction pattern formed therein or thereon, to focus or diffuse the light. The lens 1036 may be sintered or textured to provide diffusion to the light emitted.

In exemplary embodiments, a heat sink 1042 may be incorporated to dissipate heat that can build up from the light source, such as where ultraviolet light is used. In exemplary embodiments, the heat sink 1042 may be incorporated in, on or associated with the top side of the circuit board.

In exemplary embodiments, one light emitting head may incorporate blue lights and a separate head may incorporate red and/or infrared lights. In exemplary embodiments, it may be advantageous to separate the colors since more energy from the power source may be needed to energize a blue light source than may be required for a red and/or infrared light source. In other exemplary embodiments, the light emitting head may incorporate a combination of at least two of the following: red, blue, infrared, and/or ultraviolet lights or may incorporate other types or wavelengths.

In exemplary embodiments using light-emitting diodes, the light-emitting head assembly 1000 can be configured to deliver 63.333 mW/cm$^2$ total power at 3 mm from the LED plane, which equals 7.6 J per the two-minute exposure time; two thirds comes from the red LED matrix which delivers 42.222 mW/cm$^2$ and one third comes from the infrared LED matrix which delivers 21.111 mW/cm$^2$. LEDs 1030 are positioned so that concurrent spots of red and infrared light fill the area of the circuit board, generating a uniform intensity over the surface except at the fringes of the outline where some of the additive effect of neighbor LEDs is lost. The infrared LED may operate at 4 mW/Sr milliwatts per steradian) and the red LED may operate at 900 mcd ("mcd" being the abbreviation for millicandela). In exemplary embodiments, the red LED may have a minimum intensity of 900 mcd to increase total power. In one exemplary embodiment, the range may be 900-1125 mcd. Both the infrared and red LEDs may have the same half angle, and therefore the same spot size. It is to be understood that blue, white, yellow or other colors can be used.

In exemplary embodiments, the light-emitting head assembly 1000 may use blue light. In exemplary embodiments, the blue light may have nominal intensity of 40 mW/cm², with a wavelength in a range of about 400-460 nm and a total power of 1 W. In 5 minutes of application the light may delivery about 300 J of energy. Over 12 cm², the energy delivered may therefore be 25 J/cm² and may be scaled for other treatments.

In exemplary embodiments, the light-emitting head assembly 1000 may be configured to accommodate a dispensing port 910 from the fluid delivery system 900, such as by an opening in each of the connection plate 1010, circuit board 1014 and lens 1036 through which the nozzle can be fitted. In this manner fluid and light can be delivered to the skin or other surface.

The light-emitting head assembly 1000 may be useful in light therapy. Light therapy consists of intentional exposure to light using lasers, light-emitting diodes, fluorescent lamps, dichroic lamps or very bright, full-spectrum light, usually controlled with various devices, and administered for a prescribed amount of time. Light therapy can be used to treat various skin conditions, including psoriasis, acne, and eczema. Additionally, light treatment may help to reduce pore size, increase the skin's moisture retention and elasticity, and smooth the texture of aged and sun-damaged skin. In exemplary embodiments for use such in treating acne, blue light may be advantageous, whereas red and/or infrared light may be advantageous for anti-aging, skin rejuvenation and similar applications.

In exemplary embodiments, the present device may include a hair removal head assembly which may be useful in removing unwanted hair. A hair removal head assembly may include, in exemplary embodiments, a head construction similar to that of exemplary brush head assemblies as described herein, but each protrusion may be or include a portion that is a coil, the coil being made of metal, plastic or other material. Alternatively, each protrusion may be or include a portion that is a spring, such as a twisted metal spring. Alternatively, the protrusion may be or include a portion that is a thread or threadlike material, such as, but not limited to, cotton, such as that used with eyebrow or other facial hair threading. In use, as the protrusions move one or more hairs will be caught in the coil, spring, or the like and removed at the roots.

The present device can also have head assemblies combining two or more features of the aforementioned heads. For example, but not by way of limitation, an oscillating plate can incorporate both protrusions (such as bristled tufts) and a microcontroller connected to at least one light source to permit skin stimulation by tactile stimulation as well as by light stimulation. In exemplary embodiments, the fluid delivery system described hereinabove can be incorporated, as well.

Figure 35:
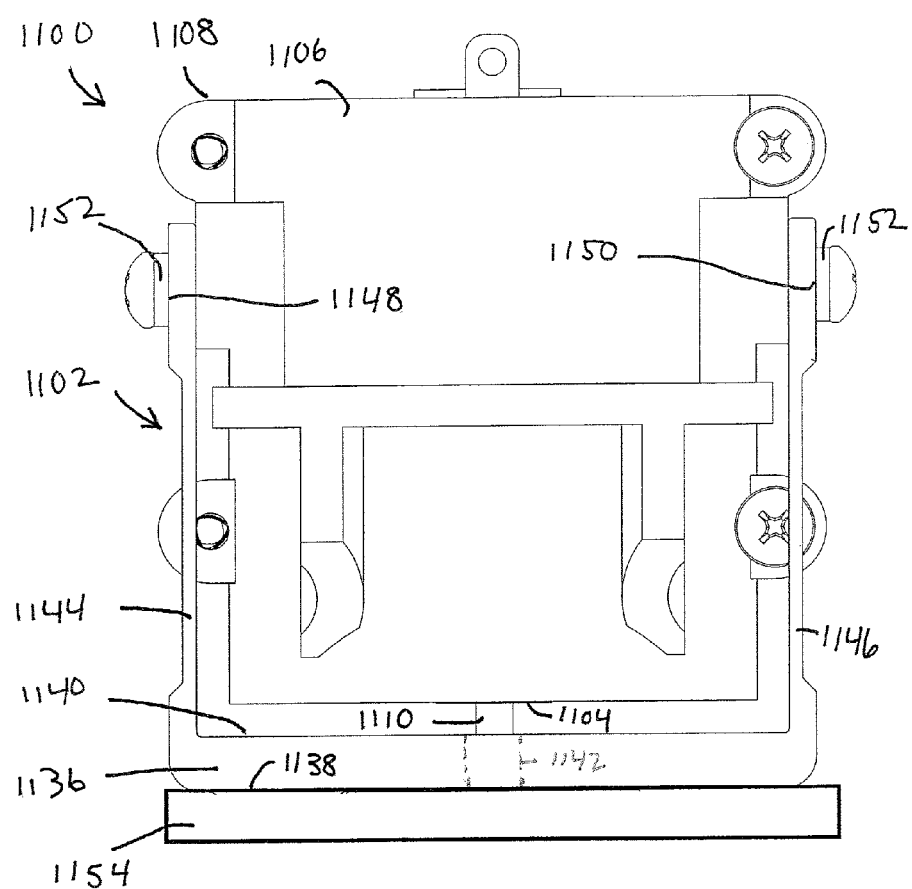
FIG. 35 is a side elevational cross-section view of an exemplary embodiment of a device incorporating a single mounting bracket and a single-lobed cam.

FIG. 35 shows an alternative exemplary embodiment of a device 1100 for producing elliptical movement incorporating a single mounting bracket 1102 and an offset cam 1104 having a single offset lobe. In exemplary embodiments, the device 1100 includes a motor 1106, optionally a motor housing 1108, and a shaft 1110 extending from the motor 1106, similar to those described hereinabove. The shaft has a central axis 1112.

Figure 36:
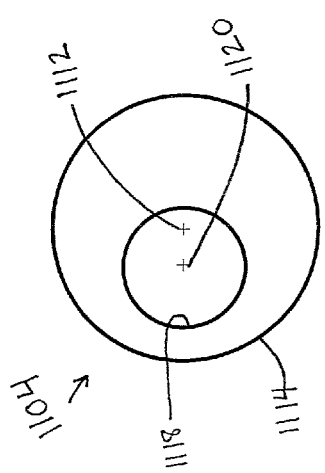
FIG. 36 is a top schematic view of a single-lobed offset axis cam.
Figure 37:
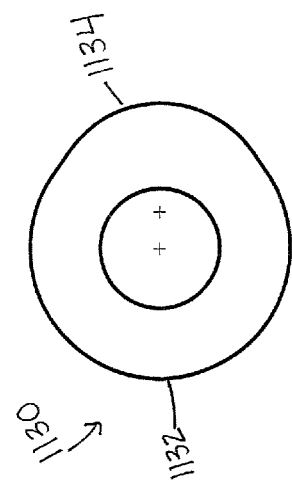
FIG. 37 is a top schematic view of a traditional cam.

The cam 1104, as shown in FIG. 36 has a circular outside circumference 1114 and has a central axis 1112. The cam 1116 also has a bore 1118 having an axis 1120 that is offset from the cam central axis 1112. In comparison to the offset axis cam 1104, a traditional cam 1130 known to those skilled in the art, shown in FIG. 37, has a circumference 1132 that is not a circle, but has a portion 1134 (shown on the right side) that protrudes beyond the geometric circle.

In alternative exemplary embodiments, rather than an offset axis cam, elliptical motion may be created by other structures, such as, but not limited to, those as described hereinabove (see, for example, the description with respect to FIGS. 7-8).

The mounting bracket 1102 has a base plate 1136 having a bottom surface 1138, a top surface 1140, a central aperture or recess 1142, and first and second arms 1144, 1146. Each arm has a connecting portion 1148, 1150 associated with the distal end of the arm. In exemplary embodiments, the connecting portion may be an aperture, a boss, a loop or mean for receiving a mating male connecting member 1152. In exemplary embodiments, each arm 1144, 1146 is associated with the motor housing 1108 via the male connecting member 1152. The male connecting member 1152 may be a screw, bolt or other fastener, or may be a pin, rod, or the like. In exemplary embodiments, the male connecting member 1152 may be a boss that receives a connecting portion boss. In an alternative exemplary embodiment, each arm 1144, 1146 may have an aperture 1142 at the distal end, the aperture having an insert (not shown) made of a low friction material.

A grommet 191 fits in the mounting bracket central aperture or recess 1142. In exemplary embodiments, the grommet 191 is constructed as described hereinabove. The cam 1104 fits at least partially in the grommet central aperture. Optionally, a bearing 76 may be fitted over at least a portion of the cam 1104 and the bearing 76 fitted at least partially in the grommet 191.

In exemplary embodiments, the mounting bracket base plate 1136 may have a circular, curved or other regular or irregular shape. In exemplary embodiments, a separate interface member 1154 may be associated with the base plate and forms an interface between the base plate 1136 and the skin or other surface to be stimulated, abraded or the like. The interface member 1154 may be permanently or removably attached to or co-formed with the base plate 1136. The interface member 1154 may be flat, curved or other regular or irregular shape. In exemplary embodiments, the interface member 1154 may have an elongated portion and may have a distal end having a rounded, flat, pointed or other shaped end. The interface member 1154 may have protrusions 700 extending from the exposed side, the protrusions 700 being similar to those described herein with respect to the oscillating plate protrusions 700. Alternatively, the interface member 1154 may have an exposed surface that has an abrasive finish or coating. Alternatively, the interface member 1154 may have a surface either bonded or removably attached thereto, such as, but not limited to, an abrasion surface. Alternatively, a removable cover may be associated with the interface member 1154 that can be replaced periodically when worn out.

Figure 38:
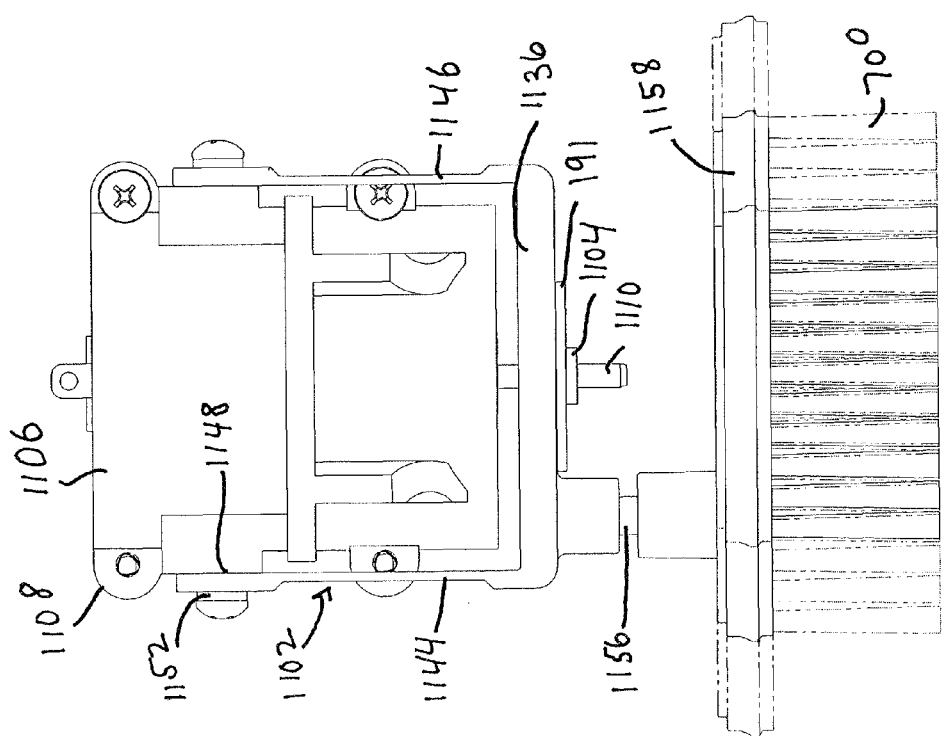
FIG. 38 is a side elevational cross-section view of an exemplary embodiment of a device to which is attached an oscillating plate with protrusions.

In exemplary embodiments, shown in FIG. 38, a connecting pin 1156 or other connecting member may permanently or detachably connect the base plate 1136 with the interface member 1154, such as, but not limited to, an oscillating plate 1158 as described hereinabove, or other structure.

Figure 39:
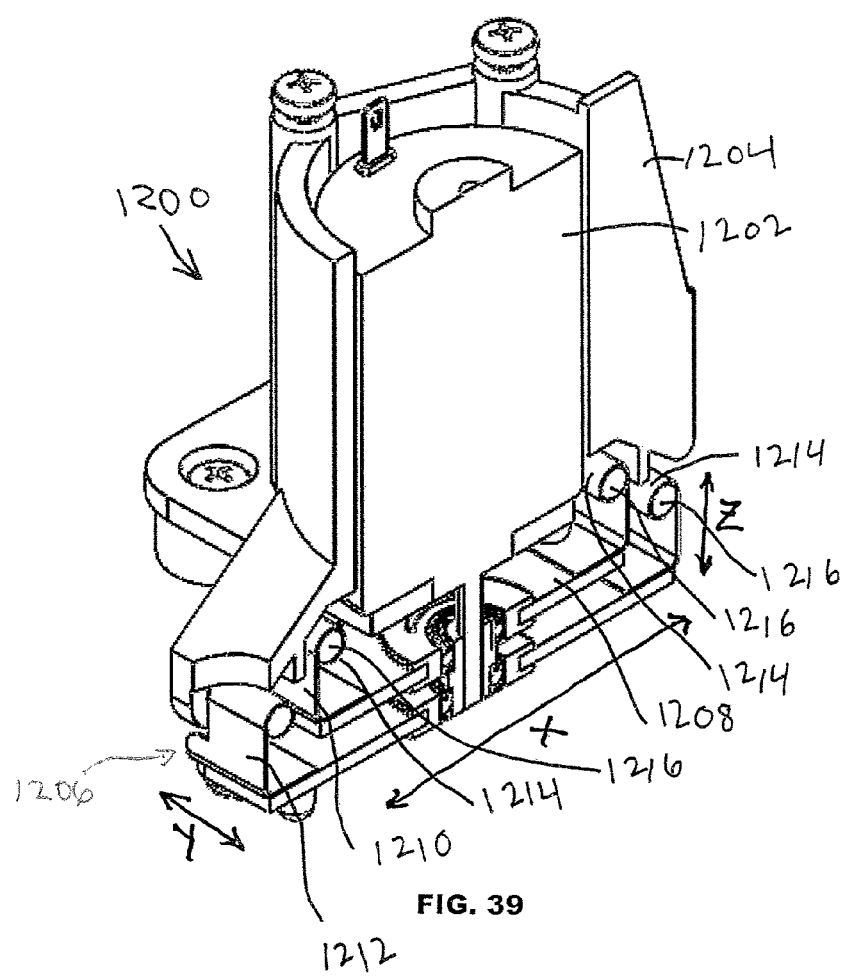
FIG. 39 is a perspective cutaway view of an exemplary embodiment of a device including motor, housing, mounting bracket and offset axis cam in which the mounting bracket arms are pivotably connected with a pair of rods associated with the motor housing.
Figure 40:
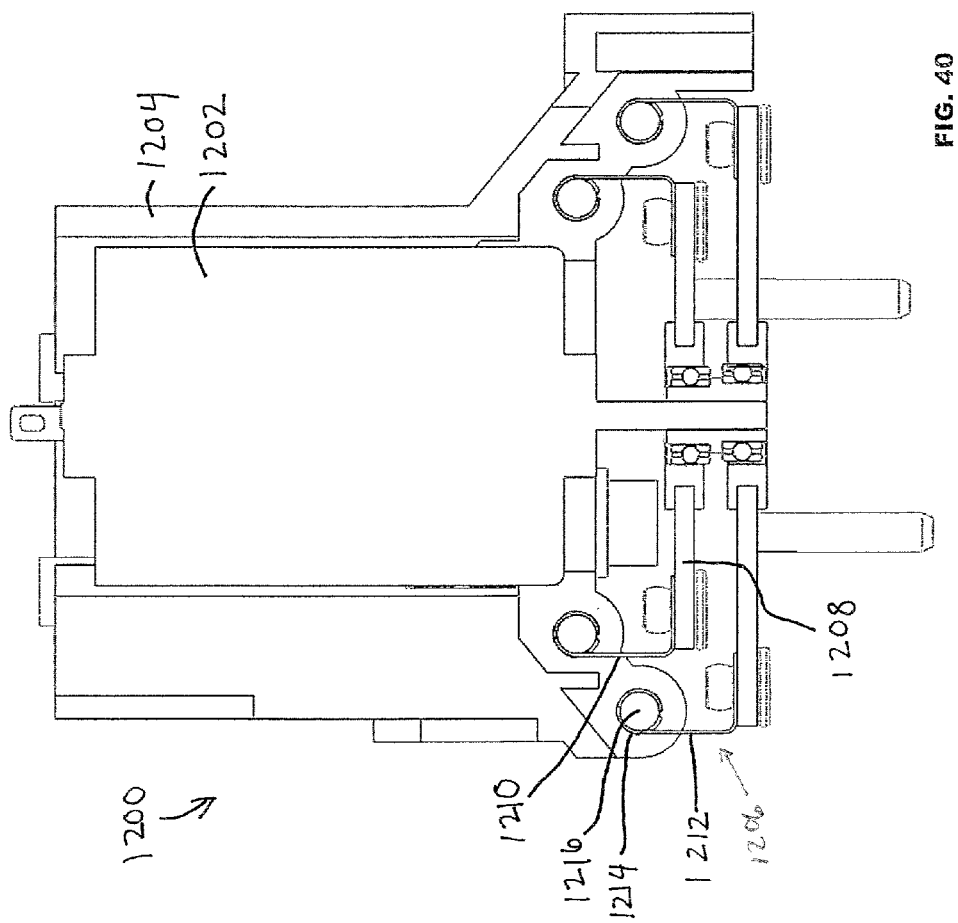
FIG. 40 is a front elevation view of the device of the exemplary embodiment of FIG. 49.
Figure 41:
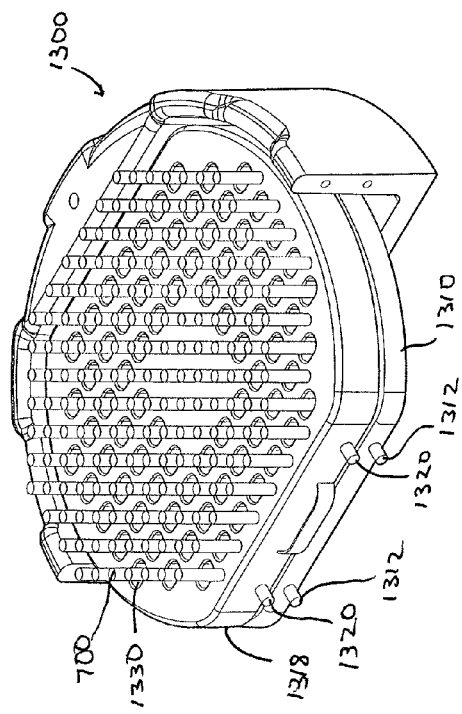
FIG. 41 is a perspective view in partial cutaway of an oscillating plate and brush head assembly housing according to an alternative exemplary embodiment showing the pins associated with the oscillating plate.
Figure 42:
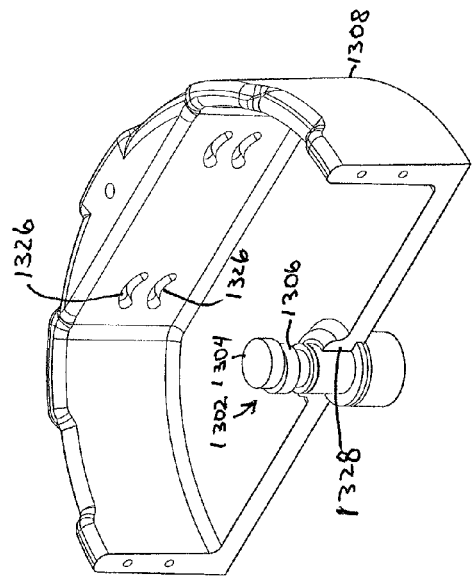
FIG. 42 is a perspective view in partial cutaway of an oscillating plate and brush head assembly housing according to the exemplary embodiment of FIG. 41 and showing the curved tracks for the pins and the offset cam.

FIGS. 39-40 show an alternative exemplary embodiment of portion of a device 1200, which includes a motor 1202, motor housing 1204 and bracket assembly 1206. A base plate 1208 includes an inner mounting bracket arm 1210 and an outer mounting bracket arm 1212 each have a distal end that terminates in a female connecting portion 1214, such as, but not limited to, a loop, aperture, bore, sleeve or the like. At least one male connecting portion 1216 such as a rod, pin, boss, tube, or the like, is associated with opposing sides of the motor housing 1204. In an alternative exemplary embodiment, the male connecting portion 1216 may protrude from or be associated with the motor itself, such as where no motor housing is included. The female connecting portion 1214 is fitted over the male connecting portion 1216 such that the female connecting portion 1214 can pivot about the male connecting portion 1216, thereby creating pivoting movement of the arms 1210, 1212 and the base plate in the X-axis. Additionally, the arms 1210, 1212 slide along the axis of male connecting portion 1216, thereby providing Y-axis movement. The combination of the X-axis pivoting and Y-axis sliding provides the elliptical movement path of the base plate 1208.

FIGS. 41-44 show an exemplary embodiment of a brush head attachment assembly 1300. A dual-lobe offset axis cam 1302 (driven by a motor 22 and shaft 24, not shown) has a first offset axis cam lobe 1304 and a second offset axis cam lobe 1306, similar to the cam described 62 hereinabove. The assembly 1300 also includes an assembly housing 1308. The assembly 1300 also includes a first oscillating plate 1310 having a pair of first pins 1312 extending from one area of the plate edge and a pair of second pins 1314 (not shown) extending from an area of the plate edge opposite from the area of the pair of first pins 1312. The first oscillating plate 1310 may have a central aperture 1316 having a grommet 191 (not shown, but as described hereinabove) associated therewith. A second oscillating plate 1318 similarly has a pair of first pins 1320 extending from one area of the plate edge and a pair of second pins 1322 (not shown) extending from an area of the plate edge opposite from the area of the pair of first pins 1320. The second oscillating plate 1318 may have a central aperture 1324 extending at least partially through the plate. The central aperture 1324 may have a grommet 191 (as described hereinabove) associated therewith. The assembly housing 1308 (a portion of which is shown in the figures) includes a track 1326 for each pin. In exemplary embodiments, the track 1326 may be curved. In exemplary embodiments, the track 1326 may be a slot or a groove in the housing 1308 and may extend through or partially through the housing. In exemplary embodiments, the track 1326 may be a raised lip extending from the housing wall. Each pin is disposed in a track. Each pin may slide along the track 1326. Each pin may slide at least partially in or out of the track 1326 (in the direction of the axis of the pin). The pins sliding along the track 1326 and in and out of the track permit X-axis and Y-axis elliptical movement of the oscillating plates 1310, 1318.

The assembly housing 1308 includes an aperture 1328 into which at least a portion of the shaft 24 and the offset axis cam 1302 fits. The assembly housing 1308 is attached to the device housing, such as, but not limited to, by pressure fit, a snap fit, screwing via mating threads in both the attachable assembly housing and the device housing, or other attachment means. Alternatively, the assembly housing 1308 may be permanently attached to the device housing, such as by gluing, welding, or the like. The cam 1302 fits in the central aperture 1328 in the assembly housing 1308. The first cam lobe 1304 fits in the central aperture 1316 in the first oscillating plate 1310 and the second cam lobe 1306 fits in the central aperture 1324 in the second oscillating plate 1318.

In exemplary embodiments, each oscillating plate has a plurality of protrusions 700 protruding from one surface of the plate that may be constructed as described hereinabove. The second oscillating plate 1318 may have rows of protrusions 700. Between adjacent rows of protrusions 700 may be rows of slots 1330. Protrusions 700 from the first oscillating plate 1310 may be disposed in the slots 1330. In exemplary embodiments, the length of the protrusions 700 of the first oscillating plate 1310 is such that the distal ends of the protrusions 700 are generally co-planar with the distal ends of the protrusions 700 of the second oscillating plate 1318. In exemplary embodiments, the protrusions 700 from both plates generally form a brush-like surface.

In exemplary embodiments, the device operates as follows. When the shaft 24 rotates and causes the cam lobes 1304, 1306 to rotate, the first cam lobe 1304 causes the first oscillating plate 1310 to move in a first elliptical path, with the pins 1320, 1314, sliding and moving within the tracks 1326. The second cam lobe 1306 causes the second oscillating plate 1318 to move in a second elliptical path, with the pins 1320, 1322 sliding and moving within the tracks 1326. The first and second elliptical paths are offset from each other. In exemplary embodiments, the offset of the paths may be 90 degrees or may be offset by other amounts.

Figure 45:
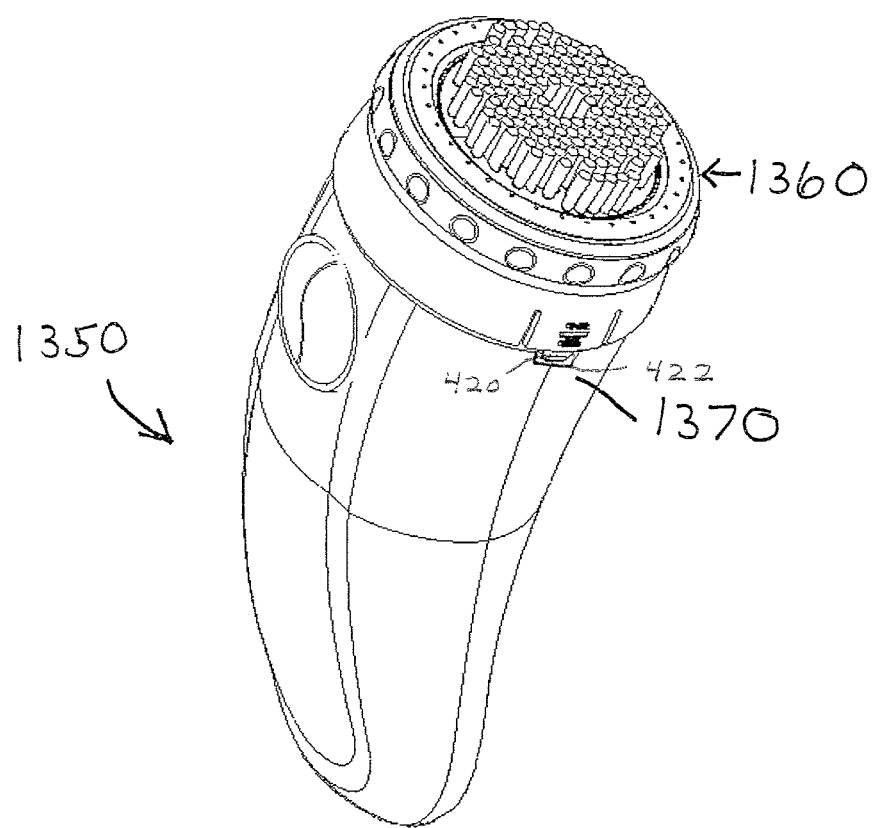
FIG. 45 is a perspective view of a device showing a brush head assembly attached to the main housing in an exemplary embodiment.

FIG. 45 is a perspective view of an exemplary embodiment of a device 1350 showing a brush head assembly 1360 attached to the main housing 1370 of the device.

Exemplary embodiments of the presently disclosed device can be adapted for use in a variety of different applications. In exemplary embodiments, the device or components thereof can be enlarged for use in cleaning carpets, floors or other surfaces where scrubbing, buffing, abrading, or other vigorous application of a moving brush, cloth or other material is typically used. In exemplary embodiments, the oscillating brush head can be enlarged to accommodate a large piece of sandpaper, buffing or other material and the device used as a sander capable of delivering elliptical movement. In other exemplary embodiments, the device can have the oscillating plate assembly miniaturized for use as, for example, a toothbrush head. In exemplary embodiments of one or more of the foregoing uses, fluid may be delivered during application of the device by a fluid delivery system incorporated in the device.

The fluid delivery system can be modified to have an external pressurized fluid source whereby the device has an actuation switch, button or other control that actuates an external pump that can force fluid through the delivery tube(s) to the oscillating plates. Such an embodiment would permit delivery of larger amounts and higher pressures of fluids.

The present disclosure also provides exemplary embodiments of methods for treating skin or other surface. In one exemplary embodiment, a method for treating skin is provided in which a device as described hereinabove is applied to the skin whereby portions of the skin are contacted by the oscillating plate or plates (or material associated therewith) as described herein in various exemplary embodiments. Alternatively, the skin may be subjected to treatment or application by one of the other head assemblies as described hereinabove.

Exemplary embodiments of the present device may be configured to provide parallel or in-series combination therapies. For example, the brush head assembly may contain protrusions for stimulation/abrasion and also contain at least one light-emitting device as described hereinabove, thereby providing stimulation, abrasion, cleansing, massage or other treatment, as well as light therapy at the same time.

Although only a number of exemplary embodiments have been described in detail above, those skilled in the art will readily appreciate that many modifications are possible in the exemplary embodiments without materially departing from the novel teachings and advantages. Accordingly, all such modifications are intended to be included within the scope of this disclosure as defined in the following claims.

While the methods, equipment and systems have been described in connection with specific embodiments, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect.

This holds for any possible non-expressed basis for interpretation, including: matters of logic with respect to arrangement of steps or operational flow; plain meaning derived from grammatical organization or punctuation; or the number or type of embodiments described in the specification.

As used in the specification and the appended claims, the singular forms "a," "an" and "the" include plural referents unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods, equipment and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods, equipment and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Any patents, applications and publications referred to herein are incorporated by reference in their entirety.

The invention claimed is:

1. An apparatus for providing elliptical motion, comprising:
   a) a motor;
   b) a drive shaft having an axis of rotation and extending from the motor, the shaft having a distal end;
   c) an elliptical motion creating mechanism associated with the shaft, the mechanism including at least one axially offset member having an axis of rotation in an axis offset from the axis of the shaft;
   d) a mounting bracket comprising
      i) a base plate operatively associated with the offset member, the base plate having a first side defining an X-axis movement direction and a second side generally perpendicular to the first side, the second side defining a Y-axis movement direction,
      ii) a first side arm extending from the base plate and associated with the motor, the first side arm having a distal end terminating in a connection portion, the first side arm defining a Z-axis movement direction,
      iii) a second side arm extending from the base plate and associated with the motor, the second side arm having a distal end terminating in a connection portion; and,
   e) a second axially offset member and a second mounting bracket, the second mounting bracket comprising
      i) a base plate operatively associated with the offset member, the base plate having a first side defining an X-axis movement direction and a second side generally perpendicular to the first side, the second side defining a Y-axis movement direction,
      ii) a first side arm extending from the base plate and associated with the motor, the first side arm having a distal end terminating in a connection portion, the first side arm defining a Z-axis movement direction, and
      iii) a second side arm extending from the base plate and associated with the motor, the second side arm having a distal end terminating in a connection portion,
   wherein the second mounting bracket is associated with the second offset member such that the first and second mounting brackets are adapted to each move in a separate and offset elliptical path, and
   whereby rotation of the shaft causes the offset members to rotate and impart elliptical motion to the mounting brackets such that the base plates move in an elliptical path in both the X-axis and Y-axis directions.

2. An apparatus for providing elliptical motion, comprising:
   a) a housing;
   b) a motor;
   c) a drive shaft having an axis of rotation and extending from the motor;
   d) at least one attachment member associated with the motor;
   e) an elliptical motion creating mechanism associated with the shaft, the mechanism including a first offset motion means for imparting movement in a first rotational direction offset from the axis of the shaft and a second offset motion means for imparting movement in a second rotational direction offset from the axis of the shaft; and,
   f) a mounting bracket assembly comprising
      i) an inner mounting bracket comprising
         (a) an inner base plate operatively associated with the first offset motion means of the elliptical motion creating mechanism, (b) a first side arm extending from the inner base plate and associated with an attachment member,
(c) a second side arm extending from the inner base plate and associated with an attachment member,
(d) a first pin extending from the inner mounting bracket base plate, ii) an outer mounting bracket comprising,
(a) an outer base plate operatively associated with the second offset motion means of the elliptical motion creating mechanism,
(b) a first side leg extending from the outer mounting bracket base plate,
(c) a second side leg extending from the outer mounting bracket base plate,
(d) a second pin extending from the outer mounting bracket base plate, whereby rotation of the shaft causes the first offset motion means for imparting movement to rotate and impart oscillating elliptical motion to the inner mounting bracket and the first pin, and impart oscillating elliptical motion to the outer mounting bracket and the second pin.

3. The apparatus of claim 2, further comprising
a) a first oscillating plate having a first face operatively associated with the first pin; and,
b) a second oscillating plate having first face operatively associated with the second pin, wherein the first and second plates are in separate generally parallel planes,
whereby when the motor is actuated, the first oscillating plate moves in a first elliptical path and the second oscillating plate moves in a second elliptical path that is offset from the first elliptical path.

4. The apparatus of claim 3, further comprising a plurality of protrusions extending from a second face of each oscillating plate.

5. The apparatus of claim 4, wherein at least a portion of the protrusions comprise tufts of bristles.

6. The apparatus of claim 4, wherein at least a portion of the protrusions comprise rods having a degree of flexibility.

7. The apparatus of claim 4, wherein at least one of the protrusions comprises a rod have a distal end having a shape selected from the group consisting of flat, rounded, beveled, tapered, conical, pointed, ball-ended, concave curved, convex curved, and recessed.

8. The apparatus of claim 4, wherein at least a portion of the protrusions have a material either coated on or impregnated in at least a portion of the protrusion.

9. The apparatus of claim 4, wherein at least a portion of the protrusions can retain fluid.

10. The apparatus of claim 9, whereby the first and second oscillating plates are in separate generally parallel planes and the distal ends of the first oscillating plate protrusions and the distal ends of the second oscillating plate protrusions are generally co-planar.

11. The apparatus of claim 3, wherein the first oscillating plate and the second oscillating plate are curved.

12. The apparatus of claim 11, whereby when the motor is actuated, the protrusions of the first oscillating plate oscillate in a first elliptical path and the protrusions of the second oscillating plate oscillate in a second elliptical path, whereby the first elliptical path and the second elliptical path are offset from one another.

13. The apparatus of claim 12, wherein the first elliptical path and the second elliptical path are offset from one another by 90 degrees.

14. The apparatus of claim 3, wherein the second oscillating plate has a plurality of rows of protrusions and a plurality of elongated slots, each slot being defined between adjacent rows of protrusions, and wherein the first oscillating plate has rows of protrusions, whereby at least one of the first oscillating plate protrusions in a given row is adapted to be received in an elongated slot.

15. The apparatus of claim 3, wherein the first oscillating plate and second oscillating plate elliptically move in separate distinct and generally parallel planes.

16. The apparatus of claim 2, wherein the elliptical motion creating mechanism comprises a cam operatively associated with the shaft, the cam having a first offset cam and a second offset cam, the first offset cam being offset from the second offset cam.

17. The apparatus of claim 2, wherein the elliptical motion creating mechanism further comprises
a) a third offset motion means for imparting movement in a third rotational direction offset from the axis of the shaft and the axes of the first and second offset motion means, and
b) a third mounting bracket comprising
i) a third base plate operatively associated with the third offset motion means of the elliptical motion creating mechanism,
ii) a first side arm extending perpendicularly from the third base plate and associated with an attachment member associated with the motor,
iii) a second side arm extending perpendicularly from the third base plate and associated with an attachment member associated with the motor,
iv) a third pin extending from the third base plate,
whereby the third mounting bracket is positioned at least partially around the outer mounting bracket and whereby the first, second and third pins are generally co-parallel.

18. The apparatus of claim 2, further comprising an attachment head assembly either detachably or permanently associated with the housing, the attachment head assembly comprising,
a) a first oscillating plate having a first face operatively associated with the first pin; and,
b) a second oscillating plate having a first face operatively associated with the second pin, wherein the first and second oscillating plates are in separate generally parallel planes,
c) a head assembly housing,
d) a first suspension ring associated with first oscillating plate and the head assembly housing such that the first suspension ring permits movement of the first oscillating plate in an X-axis, a Y-axis and a Z-axis,
e) a second suspension ring associated with second oscillating plate and the head assembly housing such that the second suspension ring permits movement of the second oscillating plate in an X-axis, a Y-axis and a Z-axis.

19. The apparatus of claim 18, wherein the first oscillating plate has a first boss extending from the first face and is associated with the first pin and the second oscillating plate has a second boss extending from the first face and is associated with the second pin, whereby when the motor is actuated, the first oscillating plate moves in a first elliptical path and the second oscillating plate moves in a second elliptical path that is offset from the first elliptical path.

20. The apparatus of claim 19, wherein the first oscillating plate comprises two plate segments, each segment adapted to attach to each other.

21. The apparatus of claim 2, further comprising an attachment head assembly either detachably or permanently associated with the apparatus, the attachment head assembly comprising, a) a first oscillating plate having a first face operatively associated with the first pin, a first side edge portion having a first hinge member extending therefrom and terminating in a first attachment member, a second side edge portion having a second hinge member extending therefrom and terminating in a second attachment member, the first and second attachment members being generally parallel;

b) a second oscillating plate having first face operatively associated with the second pin, a first side edge portion having a first hinge member extending therefrom and terminating in a first attachment member, a second side edge portion having a second hinge member extending therefrom and terminating in a second attachment member, the first and second attachment members being generally parallel; and, c) a head attachment assembly housing, the housing being associated with the first oscillating plate first and second attachment members, the head attachment assembly housing further being associated with the second oscillating plate first and second attachment members, wherein each of the first and second attachment members can axially slide in the head attachment assembly housing to provide a Y-axis movement component, wherein the first and second attachment members of the first and second oscillating plates, respectively, are adapted to permit pivoting movement of the hinge member and providing an X-axis movement component, and wherein the first and second oscillating plates are in separate generally parallel planes.

22. The apparatus of claim 2,
a) wherein each of the inner mounting bracket first and second side arms and the outer mounting bracket first and second side legs terminate in a female connecting portion, and
b) further comprising a pair of first male connecting members extending from the housing and a pair of second male connecting members extending from the housing, whereby the first male connecting members receive the female connecting portion of the inner mounting bracket first and second side arms and whereby the second male connecting members receive the female connecting portion of the outer mounting bracket first and second side legs such that the inner mounting bracket first and second side arms and the outer mounting bracket first and second side legs can pivot and slide about the first and second male connecting members.

23. The apparatus of claim 22, wherein the inner mounting bracket has a first oscillating plate associated therewith and the outer mounting bracket has a second oscillating plate associated therewith.

24. The apparatus of claim 2, further comprising a light-emitting attachment assembly either detachably or permanently associated with the apparatus, the light-emitting attachment assembly comprising
a) an attachment assembly housing,
b) a circuit board associated with the attachment assembly housing,
c) at least one light-emitting device associated with the circuit board, and,
d) an electrical connection member for electrically associating the circuit board with the motor.

25. The apparatus of claim 24, further comprising a connection plate associated with the attachment assembly housing.

26. The apparatus of claim 24, further comprising a lens associated with the attachment assembly housing.

27. The apparatus of claim 24, further comprising at least one first electrical contact adapted to be electrically associated with at least one second electrical contact associated with the motor.

28. The apparatus of claim 24, further comprising a microcontroller associated with the circuit board and adapted to control the at least one light-emitting device.

29. The apparatus of claim 24, wherein the at least one light-emitting device is at least one device selected from the group consisting of an incandescent lamp, an LED lamp, an optical fiber, an infrared light-emitting device, and an ultraviolet light-emitting device.

30. A brush head assembly attachable to a drive apparatus, the drive apparatus comprising a housing, motor, drive shaft, means for producing oscillating elliptical motion in a X-axis and a Y-axis, both axes being orthogonal to the drive shaft, a first connecting member and a second connecting member, each connecting member being associated with the means for producing elliptical motion, the brush head assembly comprising:
a) a first oscillating plate having a first face including a connecting portion adapted to connect to the first connecting member, the first oscillating plate having a second face including a plurality of protrusions;
b) a second oscillating plate having a first face including a connecting portion adapted to connect to the second connecting member, the second oscillating plate having a second face including a plurality of protrusions, wherein the first and second oscillating plates are in separate generally parallel planes and adapted for oscillating elliptical motion;
c) a brush head assembly housing adapted to attach to the drive apparatus housing;
d) a first suspension ring associated with the first oscillating plate and the brush head assembly housing such that the first suspension ring permits movement of the first oscillating plate in the X- and Y-axes,
e) a second suspension ring associated with the second oscillating plate and the brush head assembly housing such that the second suspension ring permits movement of the second oscillating plate in the X- and Y-axes.

31. The apparatus of claim 30, wherein the first and second suspension rings are each made of an elastic material.

32. The apparatus of claim 30, wherein the first and second suspension rings each include at least one annular pleat, fold, undulation, involution or wavy cross-section shape.

33. An apparatus for skin cleansing or delivery of skin treatment, comprising:
a) a main housing;
b) a motor;
c) a drive shaft having an axis of rotation and extending from the motor;
d) at least one attachment member associated with the motor;
e) an elliptical motion creating mechanism associated with the shaft, the mechanism including a first axially offset member for imparting movement in a first elliptical direction offset from the axis of the shaft and a second axially offset member for imparting movement in a second elliptical direction offset from the axis of the shaft; and,
f) a mounting bracket assembly comprising
i) an inner mounting bracket comprising
(a) an inner base plate operatively associated with the first offset member,
(b) a first side arm extending from the inner base plate and associated with an attachment member, (c) a second side aim extending from the inner base plate and associated with an attachment member,
(d) a first pin extending from the inner mounting bracket base plate,
ii) an outer mounting bracket comprising,
(a) an outer base plate operatively associated with the second offset member,
(b) a first side leg extending from the outer mounting bracket base plate,
(c) a second side leg extending from the outer mounting bracket base plate,
(d) a second pin extending from the outer mounting bracket base plate, whereby rotation of the shaft causes the first offset member to rotate and impart oscillating elliptical motion to the inner mounting bracket and the first pin, and impart oscillating elliptical motion to the outer mounting bracket and the second pin;
g) a brush head assembly attachable to the main housing, the brush head assembly comprising
i) a first oscillating plate having a first face including a connecting portion adapted to connect to a first connecting member associated with the elliptical motion creating mechanism, the first oscillating plate having a second face including a plurality of protrusions;
ii) a second oscillating plate having a first face including a connecting portion adapted to connect to a second connecting member associated with the elliptical motion creating mechanism, the second oscillating plate having a second face including a plurality of protrusions, wherein the first and second oscillating plates are in separate generally parallel planes and adapted for oscillating elliptical motion;
iii) a brush head assembly housing adapted to attach to the main housing;
iv) a first suspension ring associated with the first oscillating plate and the brush head assembly housing such that the first suspension ring permits movement of the first oscillating plate in an X-axis and a Y-axis,
v) a second suspension ring associated with the second oscillating plate and the brush head assembly housing such that the second suspension ring permits movement of the second oscillating plate in an X-axis and a Y-axis.

34. The apparatus of claim 33, further comprising a timer for deactivating the motor after a period of time.

35. The apparatus of claim 33, further comprising a battery.

36. The apparatus of claim 35, further comprising a means for charging the battery.

37. The apparatus of claim 33, further comprising a means for connecting the apparatus to a power source.

38. The apparatus of claim 33, further comprising a fluid delivery system comprising,
a) at least one fluid reservoir,
b) at least one conduit for conveying fluid and in fluid communication with the at least one fluid reservoir,
c) at least one fluid delivery port in fluid communication with the at least one fluid reservoir, and,
d) at least one means for urging fluid from the at least one fluid reservoir toward the at least one fluid delivery port.

39. The apparatus of claim 38, wherein the at least one fluid delivery port comprises at least one manifold and at least one nozzle.

40. An apparatus for providing dual offset elliptical motion, comprising:
a) a main housing;
b) a motor;
c) a rotatable drive shaft having an axis of rotation and extending from the motor;
d) an offset axis cam associated with the shaft, the cam including a first cam lobe for imparting movement in a first elliptical direction offset from the axis of the shaft and a second cam lobe for imparting movement in a second elliptical direction offset from the axis of the shaft;
e) an attachable assembly comprising
i) an assembly housing,
ii) a first oscillating plate having a central aperture, an edge and a pair of first pins extending from a first area of the first oscillating plate edge and a pair of second pins extending from an area of the first oscillating plate edge opposite from the first area,
iii) a second oscillating plate having a central aperture, an edge and a pair of first pins extending from a first area of the second oscillating plate edge and a pair of second pins extending from an area of the second oscillating plate edge opposite from the first area,
iv) a plurality of slots either formed in or associated with the assembly housing, each slot adapted to slidingly receive one of the pins,
wherein the first cam lobe is received within the first oscillating plate central aperture and the second cam lobe is received within the second oscillating plate central aperture such that rotation of the first cam lobe causes the first oscillating plate to move in a first elliptical path and rotation of the second cam lobe causes the second oscillating plate to move in a second elliptical path, whereby the first elliptical path is offset from the second elliptical path.

\* \* \* \* \*